(12) United States Patent
Kammerer et al.

(10) Patent No.: US 6,932,759 B2
(45) Date of Patent: Aug. 23, 2005

(54) SURGICAL INSTRUMENT AND METHOD FOR TREATING FEMALE URINARY INCONTINENCE

(76) Inventors: Gene W. Kammerer, 14 Stephens Dr., East Brunswick, NJ (US) 08816; Brian Luscombe, 51 Vollers Dr., Branchburg, NJ (US) 08876; Hans-Jochen Hoepffner, Beim Reihergehoelz 6A, 25355 Barmstedt (DE); Susanne Landgrebe, Zuckerhut 3, 23867 Sulfeld (DE); Ulf Ulmsten, Ridvagen 18D, Dandervd (SE), S-18235; Jorn Lehe, Loosduinse Weg 153, The Hague (NL); Laura Angelini, 9700040 Colle Romito Ardea, Rome (IT)

( * ) Notice: Subject to any disclaimer, the term of this patent is extended or adjusted under 35 U.S.C. 154(b) by 62 days.

(21) Appl. No.: 10/285,281

(22) Filed: Oct. 31, 2002

(65) Prior Publication Data
US 2003/0149440 A1 Aug. 7, 2003

Related U.S. Application Data

(63) Continuation-in-part of application No. 09/873,571, filed on Jun. 4, 2001, which is a continuation-in-part of application No. 09/521,801, filed on Mar. 9, 2000, now Pat. No. 6,273,852.
(60) Provisional application No. 60/138,231, filed on Jun. 9, 1999.

(51) Int. Cl.[7] .............................. A61F 2/00; A61B 17/34
(52) U.S. Cl. ........................................... 600/30; 606/185
(58) Field of Search ............................... 600/30, 29, 37; 128/898; 606/144, 148, 145, 146, 167, 151, 139, 232, 72; 57/243; 602/44

(56) References Cited

U.S. PATENT DOCUMENTS 3,182,662 A   5/1965  Shirodkar
3,212,502 A  10/1965  Myers
3,311,110 A   3/1967  Singerman
3,372,695 A   3/1968  Beliveau et al.
3,472,232 A  10/1969  Earl
3,608,095 A   9/1971  Barry
3,763,860 A  10/1973  Clarke (Continued)

FOREIGN PATENT DOCUMENTS

| AU | B278089 | 9/1967 |
| AU | B441561 | 10/1973 |
| DE | 3223153 | 8/1983 |
| DE | 42 20 283 A1 | 12/1993 |
| DE | 4334419 | 4/1995 |
| EP | 0941712 | 9/1959 |
| EP | 0598976 | 6/1994 |

(Continued)

OTHER PUBLICATIONS

Co-pending appln. "Method and Apparatus for adjusting Flexible Areal Polymer Implants", Ser. No. 09/289,242 filed Jun. 7, 2000, Inventor: Jorg Priewe, et al.

(Continued)

*Primary Examiner*—Eric F. Winakur
*Assistant Examiner*—Nikita R. Veniaminov

(57) ABSTRACT

Described is a surgical instrument and method for treating female urinary stress incontinence. The instrument includes a first curved needle-like element defining in part a curved shaft having a distal end and a proximal, a tape, or mesh, for implanting into the lower abdomen of a female to provide support to the urethra; a second curved needle element having a proximal end and a distal end, and a coupler for simultaneous attachment to the distal end of the first needle and the distal end of the second needle. In an alternate embodiment, the second curved needle is an anesthesia needle and the method includes anesthetizing the needle pathway through a patient's body to facilitate the passage of the first needle and mesh therethrough.

16 Claims, 44 Drawing Sheets

U.S. PATENT DOCUMENTS

| | | | |
|---|---|---|---|
| 3,858,783 A | 1/1975 | Kapitanov et al. | |
| 3,924,633 A | 12/1975 | Cook et al. | |
| 4,037,603 A | 7/1977 | Wendorff | |
| 4,128,100 A | 12/1978 | Wendorff | |
| 4,235,238 A | 11/1980 | Ogiu et al. | |
| 4,392,495 A | 7/1983 | Bayers | |
| 4,441,497 A | 4/1984 | Paudler | |
| 4,509,516 A | 4/1985 | Richmond | |
| 4,549,545 A | 10/1985 | Levy | |
| 4,946,467 A | 8/1990 | Ohi et al. | |
| 5,013,292 A | 5/1991 | Lemay | |
| 5,032,508 A | 7/1991 | Naughton et al. | |
| 5,080,667 A | 1/1992 | Chen et al. | |
| 5,112,344 A | 5/1992 | Petros | |
| 5,180,385 A | 1/1993 | Sontag | |
| 5,250,033 A | 10/1993 | Evans et al. | |
| 5,281,237 A | 1/1994 | Gimpelson | |
| 5,337,736 A | 8/1994 | Reddy | |
| 5,362,294 A | 11/1994 | Seitzinger | |
| 5,368,595 A | 11/1994 | Lewis | |
| 5,368,756 A | 11/1994 | Vogel et al. | |
| 5,382,257 A | 1/1995 | Lewis et al. | |
| 5,383,904 A | 1/1995 | Totakura et al. | |
| 5,403,328 A | 4/1995 | Shallman | |
| 5,441,508 A | 8/1995 | Gazielly et al. | |
| 5,450,860 A | 9/1995 | O'Connor | |
| 5,507,796 A | 4/1996 | Hasson | |
| 5,582,188 A | 12/1996 | Benderev | |
| 5,611,515 A | 3/1997 | Benderev et al. | |
| 5,628,756 A | 5/1997 | Barker, Jr. et al. | |
| 5,645,568 A | 7/1997 | Chervitz et al. | |
| 5,741,299 A | 4/1998 | Rudt | |
| 5,816,258 A | 10/1998 | Jervis | |
| 5,836,315 A | 11/1998 | Benderev et al. | |
| 5,840,011 A | 11/1998 | Landgrebe et al. | |
| 5,855,549 A | 1/1999 | Newman | |
| 5,860,425 A | 1/1999 | Benderev et al. | |
| 5,899,909 A | 5/1999 | Claren et al. | |
| 5,899,999 A | 5/1999 | De Bonet | |
| 5,934,283 A | 8/1999 | Willem et al. | |
| 5,935,122 A | 8/1999 | Fourkas et al. | |
| 5,945,122 A | 8/1999 | Abra et al. | |
| 5,997,554 A | 12/1999 | Thompson | |
| 6,010,447 A | 1/2000 | Kardjian | |
| 6,030,393 A | 2/2000 | Corlew | |
| 6,042,534 A | 3/2000 | Gellman et al. | |
| 6,050,937 A | 4/2000 | Benderev | |
| 6,110,101 A | 8/2000 | Tihon et al. | |
| 6,117,067 A | 9/2000 | Gil-Vernet | |
| 6,221,005 B1 | 4/2001 | Bruckner et al. | |
| 6,273,852 B1 | 8/2001 | Lehe et al. | |
| 6,306,079 B1 | 10/2001 | Trabucco | |
| 6,334,446 B1 | 1/2002 | Beyar | |
| 6,382,214 B1 | 5/2002 | Raz et al. | |
| 6,406,423 B1 | 6/2002 | Scetbon | |
| 6,475,139 B1 | 11/2002 | Miller | |
| 6,491,703 B1 | 12/2002 | Ulmsten | |
| 6,605,097 B1 | 8/2003 | Lehe et al. | |
| 6,612,977 B2 | 9/2003 | Staskin et al. | |
| 6,638,210 B2 * | 10/2003 | Berger | 600/30 |
| 6,691,711 B2 | 2/2004 | Raz et al. | |
| 2001/0018549 A1 | 8/2001 | Scelbon | |
| 2001/0049467 A1 | 12/2001 | Lehe et al. | |
| 2002/0028980 A1 | 3/2002 | Thierfelder et al. | |
| 2002/0058959 A1 | 5/2002 | Gellman | |
| 2002/0077526 A1 | 6/2002 | Kammerer et al. | |
| 2002/0091373 A1 | 7/2002 | Berger | |
| 2002/0188169 A1 | 12/2002 | Kammerer et al. | |
| 2003/0004395 A1 | 1/2003 | Therin | |
| 2003/0023138 A1 | 1/2003 | Luscombe | |
| 2003/0149440 A1 | 8/2003 | Kammerer et al. | |
| 2003/0176762 A1 | 9/2003 | Kammerer | |
| 2003/0195386 A1 | 10/2003 | Thierfelder et al. | |
| 2003/0220538 A1 | 11/2003 | Jacquetin | |
| 2004/0039453 A1 | 2/2004 | Anderson et al. | |

FOREIGN PATENT DOCUMENTS

| | | |
|---|---|---|
| EP | 0688056 | 8/1995 |
| EP | 0 774 240 A1 | 5/1997 |
| EP | 1025811 | 8/2000 |
| SE | 503271 | 4/1996 |
| WO | 9003766 | 4/1990 |
| WO | 9606567 | 3/1996 |
| WO | WO 96/06597 | 3/1996 |
| WO | 9713465 | 4/1997 |
| WO | 9831301 | 7/1998 |
| WO | WO 01/06951 A1 | 2/2001 |
| WO | WO 02/28312 A1 | 4/2002 |
| WO | 0238079 | 5/2002 |
| WO | WO 2004/012626 A1 | 2/2004 |

OTHER PUBLICATIONS

Co–pending appln. "Surgical Instrumnet and Method for Treating Organ Prolapse Conditions", Ser. No. 10/359,406, filed Feb. 6, 2003, Inventor: Gene W. Kammerer (with replacement drawings).

Co–pending appln. "Surgical Instrument and Method for Treating Female Urinary Incontinence", Ser. No. 60/356, 697, filed Feb. 14, 2002, Inventor Gene W. Kammerer.

"AMS Sparc Sling System", American Medical Systems, Inc., Minnetonka, MN, 2001, pp. 1–6.

Co–pending appln. "Apparatus and Method for Treating Female Incontinence", Ser. No. 09/691,359 filed Oct. 18, 2000, Inventor Jorn Lehe et al.

Co–pending appln. "Surgical Instrument and Method for Treating Female Urinary Incontinence", Ser. No. 09/716, 546, filed Nov. 20, 2000, Inventor: Ulf Umstead, et al.

Petros, P.E. Pap, "Vault Prolapse II: Restoraton of Dynamic Vaginal Supports by Infracoccygeal Sacropexy, an Axial Day–Case Vaginal Procedure", International Urogynecol Journal, Springer–Verlag London Ltd., 2001, vol. 12, pp. 296–303.

Petros, P.E. Papa, Vault Prolapsei: "Dynamic Supports of the Vagina", International Urogynecol Journal, Springer–Vertag London Ltd., 2001, vol. 12, pp. 292–295.

"TVT Tension–free Vaginal Tape, Minimally Invasive Highly Effective Treatment for Female Stress Unrinary Incontinence", Gynecare, Ethicon, Inc., 1999, pp. 1–6.

Giberti, "Transvaginal Sacrospinous Colpopexy by Palpation–A New Minimally Invasive Procedure Using an Anchoring System,", Urology, (2001) pp. 666–668, vol. 57.

Cosson et al., "Cystocele Repair by Vaginal Patch", Progres en Urologie, (2001) pp. 340–346, vol. 11.

Collinet et al., "The Vaginal Patch Cure of Cystocele", J. Gynecol. Obstet. Biol. Reprod., (2000) pp. 197–201, vol. 29, No. 2.

Leanza et al., "New Technique for Correcting Both Incontinence and Cystocele: T.I.C.T.", Urogynaecologia International Journal (2001) pp. 133–140, vol. 15, No. 3.

* cited by examiner

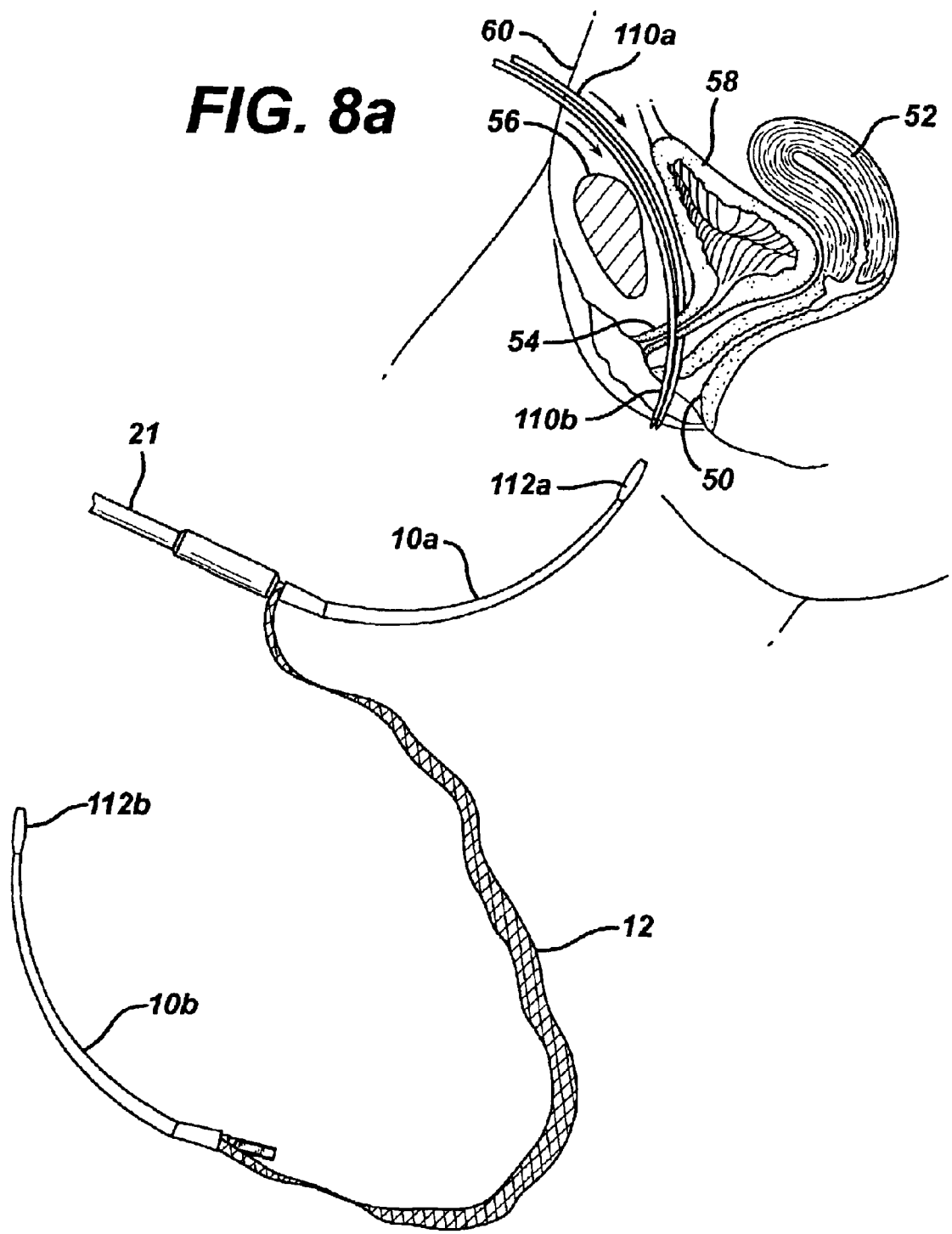

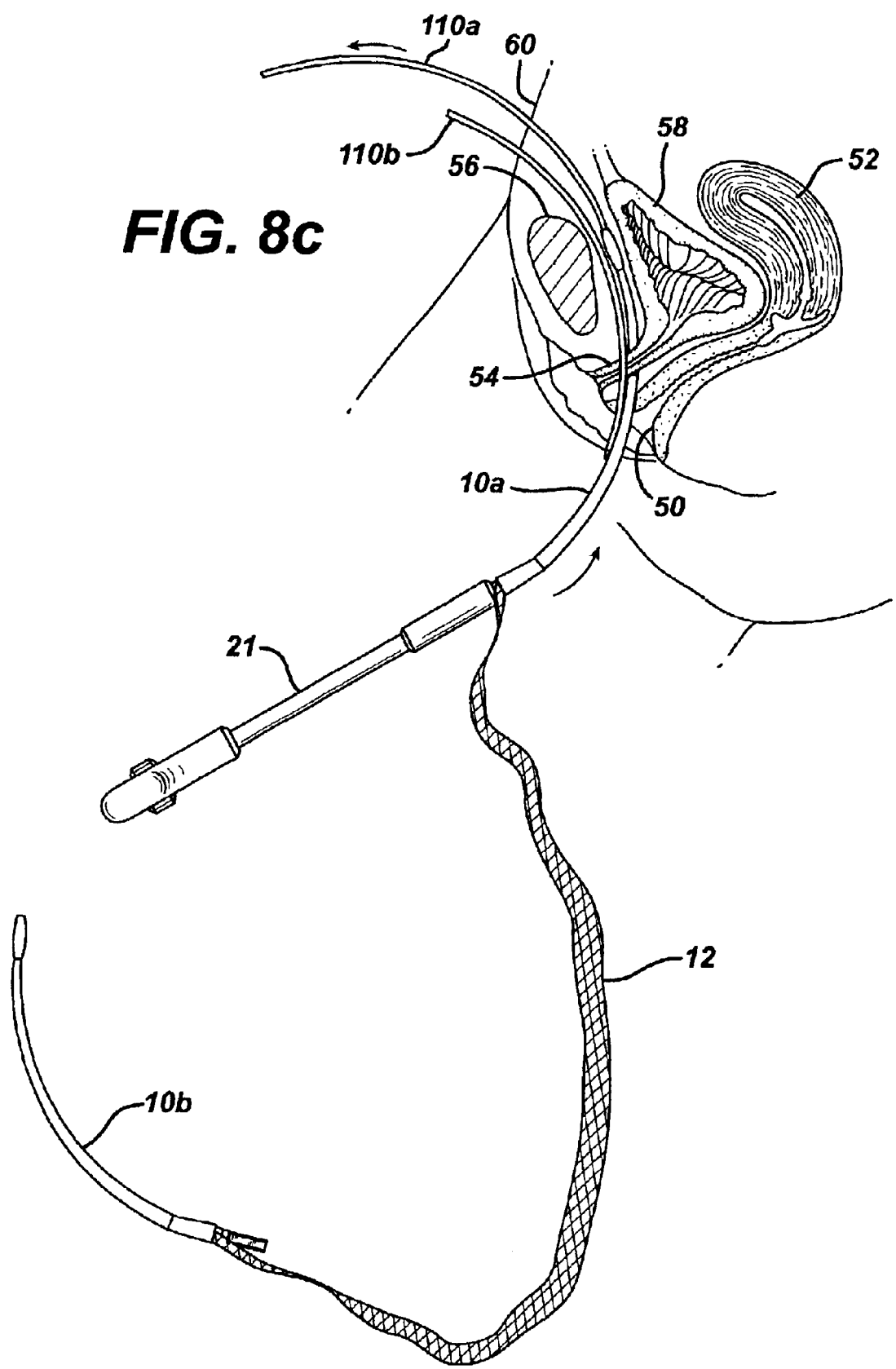

SURGICAL INSTRUMENT AND METHOD FOR TREATING FEMALE URINARY INCONTINENCE

CROSS REFERENCE TO RELATED APPLICATION

The present invention is a continuation in part of co-pending U.S. patent application Ser. No. 09/873,571, filed Jun. 4, 2001, which is a continuation-in-part of U.S. patent application Ser. No. 09/521,801, filed on Mar. 9, 2000, which issued as U.S. Pat. No. 6,273,852 on Aug. 14, 2002 and which claims the benefit of earlier-filed U.S. provisional patent application Ser. No. 60/138,231, filed on Jun. 9, 1999, all of which are hereby incorporated by reference in their entirety herein.

BACKGROUND OF THE INVENTION

1. Field of the Invention

The present invention relates generally to a surgical instrument and a method for treating female urinary incontinence and in particular to a needle and mesh configuration for creating a sling beneath the urethra.

2. Background Discussion

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise.

SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle, shying away from social situations.

U.S. Pat. No. 5,112,344 describes a method and apparatus for treating female incontinence. The surgical instrument for the application of a filamentary element into the body comprises a tubular shaft having a handle at one end and a flexible needle slidably receivable in the shaft and adapted at one end to receive a filamentary element. The method of treating female incontinence comprises looping a filamentary element between the wall of the vagina and the rectus abdominis sheath in the anterior wall of the abdomen whereby it passes to each side of the urethra, tightening the loop to bring the vaginal wall and the urethra into the correct spatial relationship to the pubis, allowing the development of scar tissue between the vaginal wall and the anterior wall of the abdomen pubic symphysis, and removing the filamentary element. During this procedure, looping of the filamentary element between the wall of the vagina and the rectus abdominis sheath in the anterior wall of the abdomen is traditionally performed while the patient is unconscious under general anesthesia. In such circumstances, the patient must be awakened before the loop is tightened so that clinical conditions and the degree of tightening that is required can be assessed.

U.S. Pat. No. 5,899,909 discloses a surgical instrument comprising a shank having a handle at one end and connecting means at the other end to receive, one at a time, two curved needle-like elements which are connected at one end to one end of a mesh intended to be implanted into the body. In practice, the mesh is passed into the body via the vagina first at one end and then at the other end, at one side and the other, respectively, of the urethra to form a loop around the urethra, located between the urethra and vaginal wall. The mesh is extended over the pubis and through the abdominal wall and is tightened. The mesh ends are cut at the abdominal wall, and the mesh is left implanted in the body. This trans-vaginal procedure is exemplified by the TVT product sold by the Gynecare franchise of Ethicon Inc., a Johnson & Johnson Company, of Somerville, N.J., USA. In this procedure two 5 mm needles pass a PROLENE mesh trans-vaginally and through the abdomen to create a tension-free support around the mid urethra. U.S. Pat. No. 5,899,909 is incorporated herein by reference in its entirety. During this procedure, implantation of the mesh to form a loop around the urethra is traditionally performed while the patient is unconscious under general anesthesia. In such conditions, the patient must be awakened before the loop is tightened so that clinical conditions and the degree of tightening that is required can be assessed.

An alternate method to treat SUI is the sling procedure. In this procedure a needle or other suture-retrieving device is first inserted through the abdomen, above the pubic bone. The needle is guided behind the pubic bone, through the subrapubic fascia around the urethra, and out of the body through an incision in the anterior vaginal wall. At this point sutures are attached to the needle(s) and pulled up back through the abdominal cavity, where the sutures are fastened to the rectus muscle.

Techniques for protecting against the puncture of the internal structures during this type of procedure have included laparoscopic procedures. This involves making an incision in the abdomen and inserting a video scope to watch the progress of the needles as they pass through the abdominal cavity. These additional incisions are not optimal for the patient. Also, the needles which pass through the abdomen are not designed to capture a mesh but rather a suture which has been previously attached to the mesh or harvested fascia. These needles are generally in the diameter range of about 0.090 ins. to about 0.120 inches. Therefore, the needles do not create a large channel through the fascia. The channel is only wide enough to pass the suture. Accordingly, the sutures do not possess the elongation properties of the PROLENE mesh and therefore can not provide the tension-free support of the TVT. Also attaching a mesh directly to these needles is not optimal because it is very difficult, if at all possible, to pull the mesh through the narrow channel created by the needle.

It would be beneficial to provide a surgical system for use in implanting a mesh within a female body to prevent incontinence that can be implanted either through a trans-vaginal approach or a trans-abdominal approach.

It would also be beneficial to provide a surgical system and method for use in implanting and adjusting a mesh within a female body to prevent incontinence that can be performed using only local anesthesia, thereby avoiding the necessity of subjecting the patient to general anesthesia.

This invention addresses that need and overcomes the deficiencies of the prior art.

SUMMARY OF THE INVENTION

The invention overcomes the deficiencies of the prior art and provides for a surgical apparatus and a method for the treatment of female stress urinary incontinence. The invention provides a surgical instrument comprising a handle at one end and connecting means at the other end to receive, one at a time, two curved needle-like elements, each of which have a blunt tip and a constant or varying diameter. The distal end of the needle comprises an interlocking coupling means for accepting a guide needle or, alternatively, a mesh.

In one embodiment each curved needle connects at its proximal end to separate ends of a mesh to be implanted within the body. A guide needle, similar in structure to a Stamey needle, is passed through the abdomen and behind the pubic bone, passes along one side of the urethra and to an incision site at the anterior vaginal wall. After the guide needle exits the body through the vagina, the guide needle couples to the distal end of the curved needle. The curved needle is then pushed back through the vagina and through the fascia, following the path of the guide needle. The curved needle and first end of the mesh pass over the pubis and through the abdominal wall. The guide, needle is again passed behind the pubic bone from the abdomen, passes along the other side of the urethra to the incision site in the vaginal wall. The guide needle again couples to the distal end of the second curved needle, which then passes through the vagina and fascia, following the second path created by the guide needle. The second end of the mesh is extended over the pubis and through the abdominal wall. The mesh ends are cut at the abdominal wall, and the mesh is left in the body, creating a tension-free support between the vaginal wall and the mid urethra.

In an alternate embodiment a curved needle is passed through the abdomen and behind the pubic bone, passes along one side of the urethra and to an incision site in the anterior vaginal wall. After the curved needle exits the body through the vagina, the distal end of the curved needle couples to one end of the mesh to be implanted within the body. The curved needle is then pulled back through the vagina and through the fascia, following the path it originally created. The curved needle and first end of the mesh pass over the pubis and out through the abdominal wall. The first end of the mesh de-couples from the curved needle and the needle is again passed behind the pubic bone from the abdomen, passes along the other side of the urethra to the incision site in the vaginal wall. The needle couples to second end of the mesh and is then pulled back through the vagina and fascia, following the second path created by the needle. The second end of the mesh is extended over the pubis and through the abdominal wall. The mesh ends are cut at the abdominal wall, and the mesh is left in the body, creating a tension-free support between the vaginal wall and the mid urethra.

In a further alternative embodiment, the guide needle is an anesthesia needle and a connecting mechanism is provided for connecting the distal end of the anesthesia needle to the distal ends of the two curved needles, one at a time, or alternatively to the ends of the mesh, one at a time, as described hereinabove. The method of this alternative embodiment includes first anesthetizing the needle pathway through the patient's body to facilitate the passage of the curved needles and mesh therethrough. The procedure may be performed, with an anesthesia needle as the guide needle used as described hereinabove, along with either two curved needles, one curved needle, or no curved needles, attached to the ends of the mesh to be implanted into the patient's body.

The invention is also compatible for use in a trans-vaginal approach as described in U.S. Pat. No. 5,899,909.

The object of the invention is to provide a surgical instrument that implants a mesh for treatment of SUI and is capable for using in a trans-vaginal or a trans-abdominal procedure.

An advantage of the invention is that it is useful across different medical specialties depending on preferred surgical approaches.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIGS. 3b–d are alternate embodiments of a connector for use in FIG. 3a;

FIGS. 8a–i diagrammatically illustrate several surgical steps of a trans-abdominal method utilizing two needles and two guide needles according to the invention to treat SUI.

DETAILED DESCRIPTION OF THE INVENTION

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways.

The invention discloses an apparatus and method for treating SUI. A mesh or tape is passed through pelvic tissue and positioned between the urethra and vaginal wall, creating a supportive sling. The mesh provides a structure means for tissue ingrowth and thereby provides a newly created body tissue supporting means for the urethra. When pressure is exerted upon the lower abdomen, such as during a cough or sneeze, the mesh provides support to the urethra, allowing it to keep its seal and prevent the unwanted discharge of urine.

Figure 1:
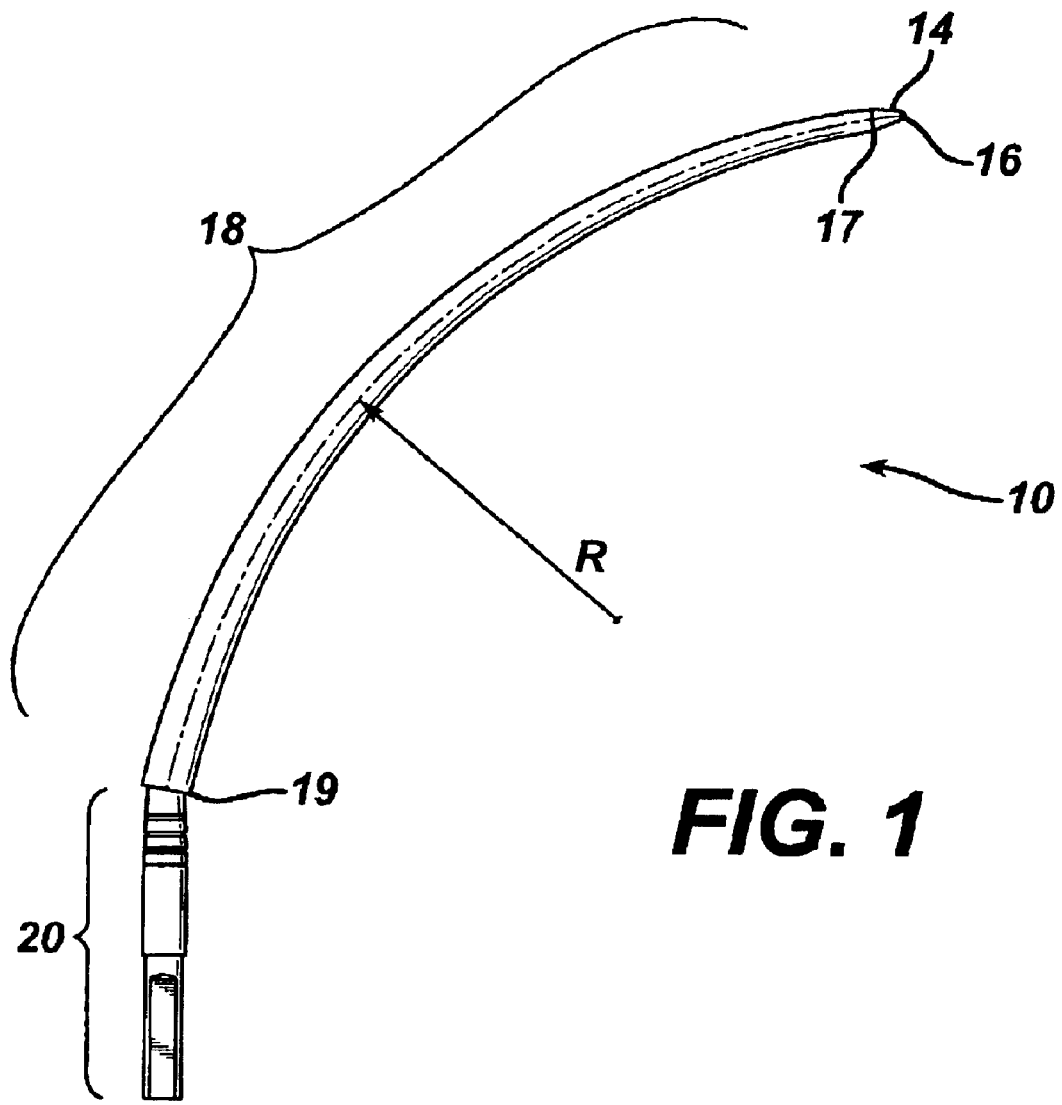
FIG. 1 is a side view of the needle in one embodiment thereof.
Figure 2A:
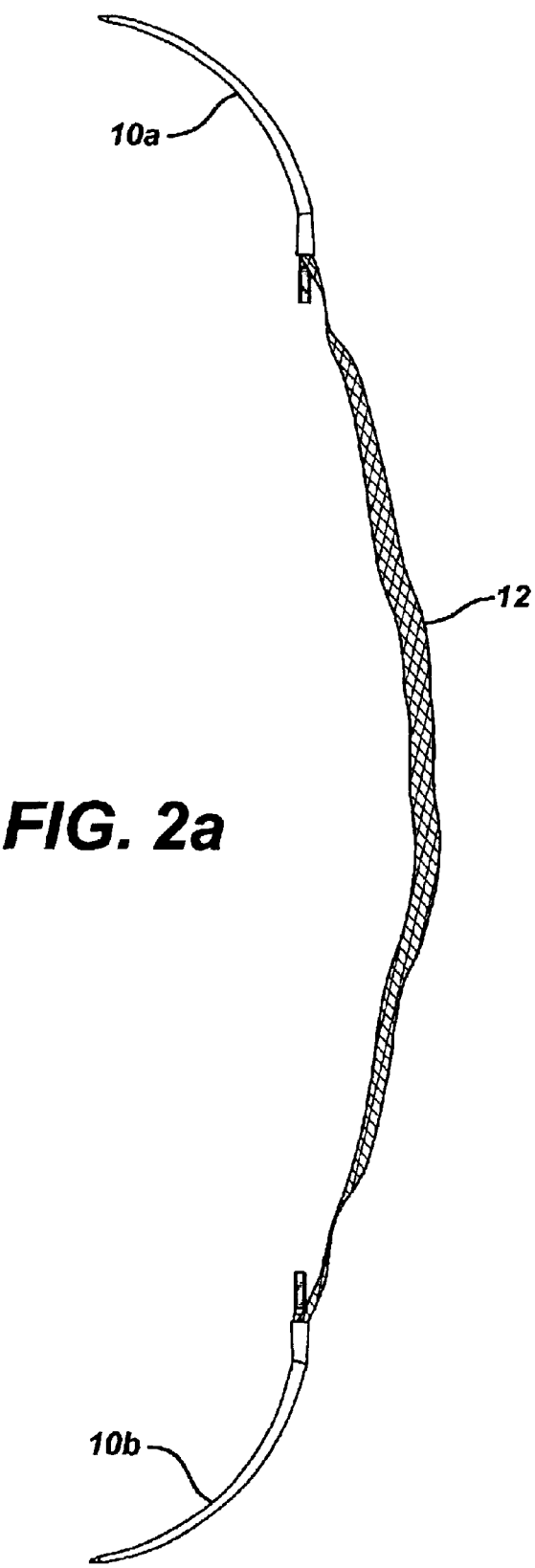
FIG. 2a is a side view of two needles and a tape, or mesh, interconnecting the needles.

Referring to FIGS. 1 and 2a, in one embodiment the surgical instrument comprises a needle-like element 10 that attaches to a mesh 12. Needle element 10 defines a certain radius R to perform the surgical procedure discussed herein. The distal end of needle element 10 terminates at a conical section 14 having a tip 16. Alternate configurations, such as a blade-like, arrow or burr tips are also possible. Preferably, tip 16 is blunt, wherein the tip 16 has a radius of about 0.6 millimeters. A blunt tip is preferred since it is less likely to stick in bone or penetrate bladder wall tissue or blood vessel wall tissue as will be appreciated from the method of implanting the mesh as described below.

The proximal end of needle 10 terminates in an attachment segment 20 that is adapted to mate and lock into a handle 21 as disclosed in U.S. Pat. No. 5,899,909.

Disposed between tip 16 and segment 20 is a curved shaft segment 18 having a distal end 17 and a proximal end 19. The shape of shaft 18 extends substantially a quarter of a circle in order to follow substantially the profile of the pubis between the vagina and the abdominal wall. For the purposes of the method as will be discussed in more detail below, shaft 18 has a preferred radius R of about 106 millimeters. The diameter of shaft 18 may be constant, for example, about 5 mm. Alternatively, the diameter of segment 18 may transition from a smaller diameter at distal end 17 to a larger diameter at proximal end 19. The minimum diameter of distal end 17 may be as small as 0.5 mm due to the minimal stresses at this point. The minimal diameter of proximal end 19 is about 4 mm.

Needle 10 is preferably tubular with a circular cross section and is made from a material that is compatible with the human body. Preferably, needle 10 is made from AISI 303 stainless steel. The surface of shaft 18 may be smooth, preferably polished, to facilitate penetration of the soft tissue. Alternatively, the surface of needle 10 may have a somewhat rougher surface. A rougher surface would result in slightly additional tissue trauma, which in turn stimulates fibroblast activity around the mesh 12. The surface of needle 10 may also be darkened in shade or color to provide higher visibility while in place in the body during a cystoscopy.

Needle 10 may be manufactured as a single, continuous unit, or alternatively, curved portion 18 may be manufactured separately from linear portion 20. In this manner the two pieces would attach using any conventional attaching means, such as, screwing, or other conventional means as is known to those skilled in the art.

Figure 2B:
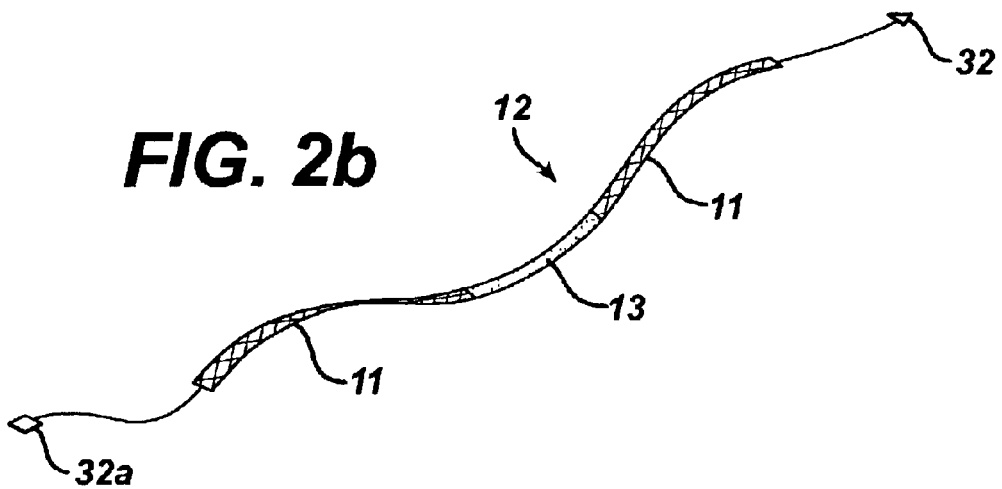
FIGS. 2b–d are alternate embodiments of the mesh and connecting means between the mesh and needle.
Figure 2C:
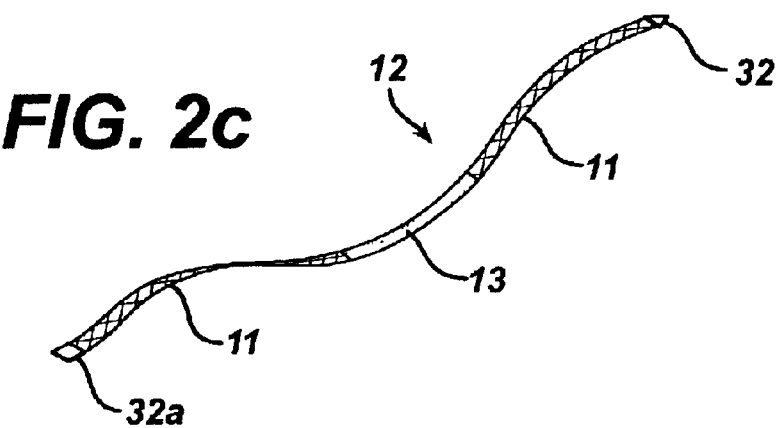
Figure 2D:
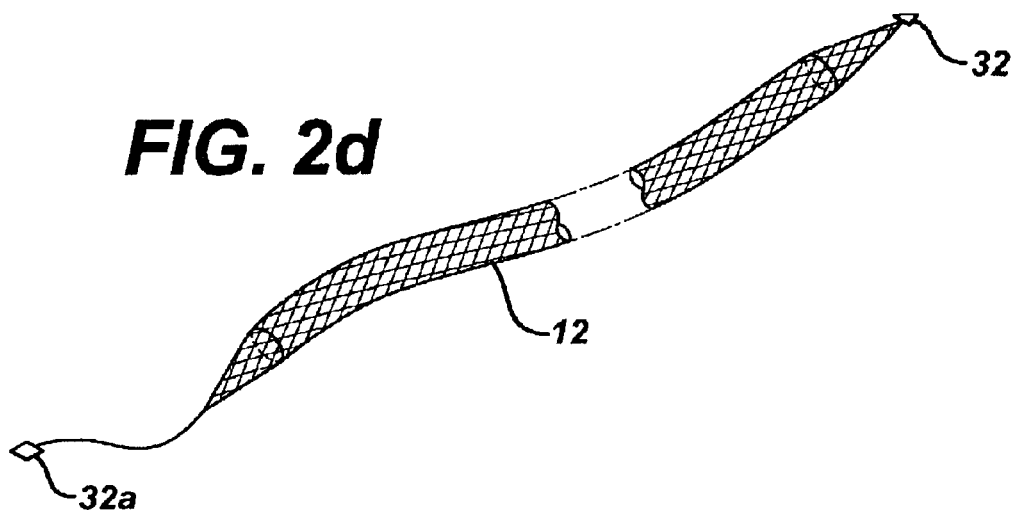

Referring to FIGS. 2a–d, mesh 12 comprises any tissue-compatible synthetic material, or any natural material, including, but not limited to, autologous, allograft, xenograft, a tissue engineered matrix, or a combination thereof. An exemplary synthetic material is PROLENE® polypropylene mesh, a mesh having a thickness of 0.7 mm and openings of about 1 mm manufactured by Ethicon, Inc., Somerville, N.J., U.S.A. This material is approved by the U.S. Food and Drug Administration for implantation into the human body. A still further embodiment of the mesh 12 is a combination of a synthetic material 11 and a natural material 13 centered between the synthetic material 11 as shown in FIGS. 2b–c. A still further embodiment of the mesh 12 includes a combination of synthetic material 11 and natural material 13, whereby the natural material is placed over or incorporated within a generally central portion of the synthetic material 11. One advantage of the mesh configurations is that natural material 13 is along the center region of mesh 12 so that after installation of mesh 12, natural material 13 is positioned below the urethra and eliminates possible erosion issues at the interface of the urethra and mesh. Natural material 13 may be connected to the synthetic material 11 by means of sewing, a bio-compatible glue, cell culturing techniques or other known means.

Mesh 12 may be of any convenient shape that suits the intended purpose of the invention. An exemplary width is about 1 cm and the length would be dependent upon the size of the female undergoing the procedure. Mesh 12 may be single or double ply, generally planar in structure, or tubular (FIG. 2d) to provide additional supporting strength and more surface area on which tissue fibers may attach. Moreover, mesh 12 may consist of different types of material, such as a bioabsorbable and non-bioabsorbable material. Mesh 12 may also be coated with an antimicrobial additive to prevent or minimize infection and a lubricous coating, for example, a bioabsorbable hydrogel, to facilitate the mesh passing through the tissue as discussed below. Preferably, mesh 12 is covered by a removal plastic sheath as disclosed in U.S. Pat. No. 5,899,909. The mesh may also be made radio-opaque and/or of a contrasting color to the body tissue to allow for future diagnostic visualization.

In one embodiment mesh 12 may be attached to needle segment 20 by means of tying, gluing or other suitable attaching means. Preferably, a bio-compatible heat shrink tube fixes mesh 12 onto needle portion 20, FIG. 2a.

Figure 3A:
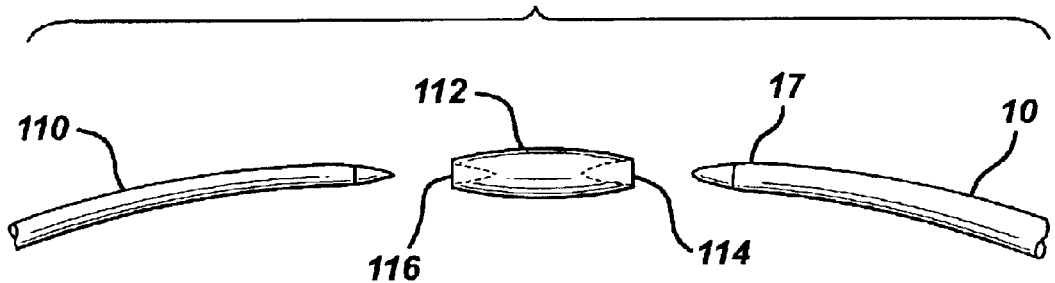
FIG. 3a is an assembly diagram for two needles and a connector.

FIG. 3a illustrates a needle 10 for use in conjunction with a guide needle 110 and coupler 112. Guide needle 110 may be configured to have a similar radius R as needle 10. Preferably, guide needle 110 has a smaller diameter, about 2 mm. It is possible, however, for guide needle 110 to have the same diameter as needle 10. A coupler 112 acts as an interfacing element useful to couple guide needle 110 to needle 10. Coupler 112 is substantially elliptical-shaped having a first bore opening 114 for accepting distal end 17 and a second bore opening 116 for accepting the distal end of guide needle 110. Preferably, openings 116 and 114 are configured to allow for a press fit connection with needles 110 and 10, respectively. Alternatively, openings 114 and 116 may comprise a bio-compatible glue or high-friction material to facilitate a strong connection between the needles 10/110 and coupler 112. Coupler 10 may be made from any bio-compatible metal, such as stainless steel or polyurethane, silicone, rubber or other similar compound.

Figure 3B:
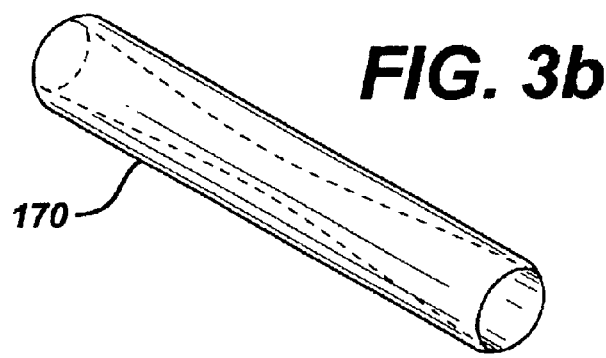
Figure 3C:
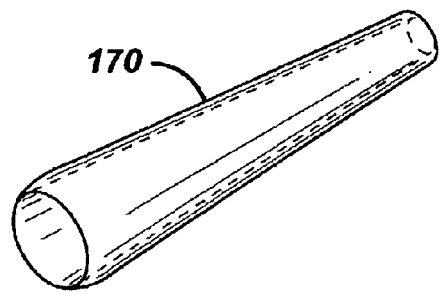
Figure 3D:
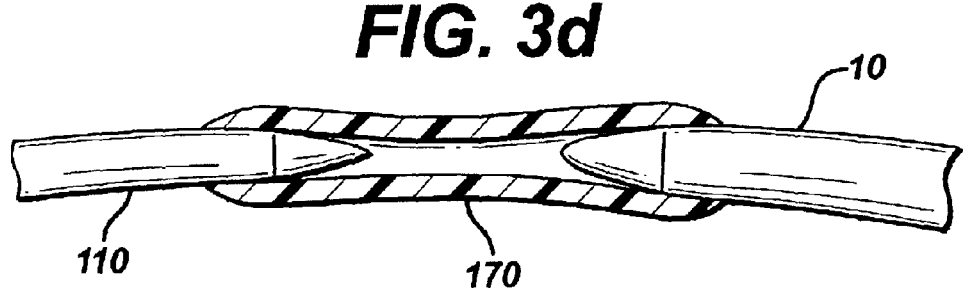

FIGS. 3b–d illustrate alternate connector means utilizing a high friction tube 170, such as Tygon. FIG. 3b discloses a tube having a constant O.D., but a varying I.D. The larger I.D. would accept needle 10 and the smaller I.D. accepts the guide needle 110. FIG. 3c illustrates a tube 172 having both a varying O.D. and I.D. As the needles are placed within the tube the decreasing I.D. compresses around the distal ends of the respective needles and the high coefficient of friction securely anchors the needles. FIG. 3d illustrates the needles within the tube 172. Preferably, the ends of tube 170 and 172 are tapered to eliminate any abrupt surface that adds additional drag to the needles as they are pulled through the abdominal cavity.

The surgical procedure for trans-abdominally implanting mesh 12 using two needles is shown in FIGS. 4a–j. In the figures the relevant parts of the female lower abdomen are disclosed, the vagina being 50, the uterus 52, the urethra 54, the pubic bone 56, the urinary bladder 58 and the abdominal wall 60. A guide needle 110 penetrates the abdominal wall 60, anterior to the pubic bone 56, FIG. 4a and follows the contour of the pubic bone 56 to one side of the urethra 54 and exits the body through an incision having been made in the anterior wall of the vagina 50. Coupler 112 attaches to the distal end of guide needle 110, extending out from the body, and needle 10a, FIG. 4b. One end of mesh 12 is attached to the proximal end of needle 10a. The surgeon then retracts guide needle 110 back through the abdomen and advances needle 10a through the vaginal incision following the same path guide needle 110 created, FIG. 4c. The needles pass through the vaginal wall and through the soft tissue on one side of the urethra 54, the needles then according to FIG. 4d being passed close to the back of the pubic bone 56, through additional layers of fat, muscle and fascia, and then out the abdominal wall 60 above the pubic bone 56. The surgeon uncouples handle 21 from the needle 10a and pulls needle 10a out of the body through the abdominal wall 60, FIG. 4e.

Guide needle 110 is disconnected from needle 10a, and the surgeon repeats the same procedure, but passing the guide needle 110 on the opposite side of the urethra 54, FIGS. 4f–j, to complete the implantation of the mesh between the mid-urethra and vaginal wall using needle 10b.

FIGS. 8a–i illustrate an alternate preferred embodiment. A first guide needle 110a penetrates the abdominal wall 60, anterior to the pubic bone 56 and follows the contour of the pubic bone 56 to one side of the urethra 54 and exits the body through an incision having been made in the anterior wall of the vagina 50. A second guide needle 110b penetrates the abdominal wall 60, anterior to the pubic bone 56 and follows the contour of the pubic bone 56 to the opposite side of the urethra 54 as guide needle 110a and exits the body through an incision having been made in the anterior wall of the vagina 50, FIG. 8a. At this point, the surgeon may perform a single cystoscopy to confirm the integrity of the bladder 58. Couplers 112a,b attach to the distal ends of needles 10a,b. Needle 10a, having one end of mesh 12 attached to the proximal end of needle 10a attaches to guide needle 110a via coupler 112a, FIG. 8b. The surgeon then retracts guide needle 110a back through the abdomen and advances needle 10a through the vaginal incision following the same path guide needle 110a created. The needles pass through the vaginal wall and through the soft tissue on one side of the urethra 54, the needles being passed close to the back of the pubic bone 56, through additional layers of fat, muscle and fascia, and then out the abdominal wall 60 above the pubic bone 56, FIGS. 8c–d. The surgeon uncouples handle 21 from the needle 10a and pulls needle 10a out of the body through the abdominal wall 60, FIG. 8e.

The surgeon repeats the same procedure, but removing guide needle 110b and advancing needle 10b on the opposite side of the urethra 54, to complete the implantation of the mesh between the mid-urethra and vaginal wall using needle 10b, FIGS. 8f–i.

Figure 5A:
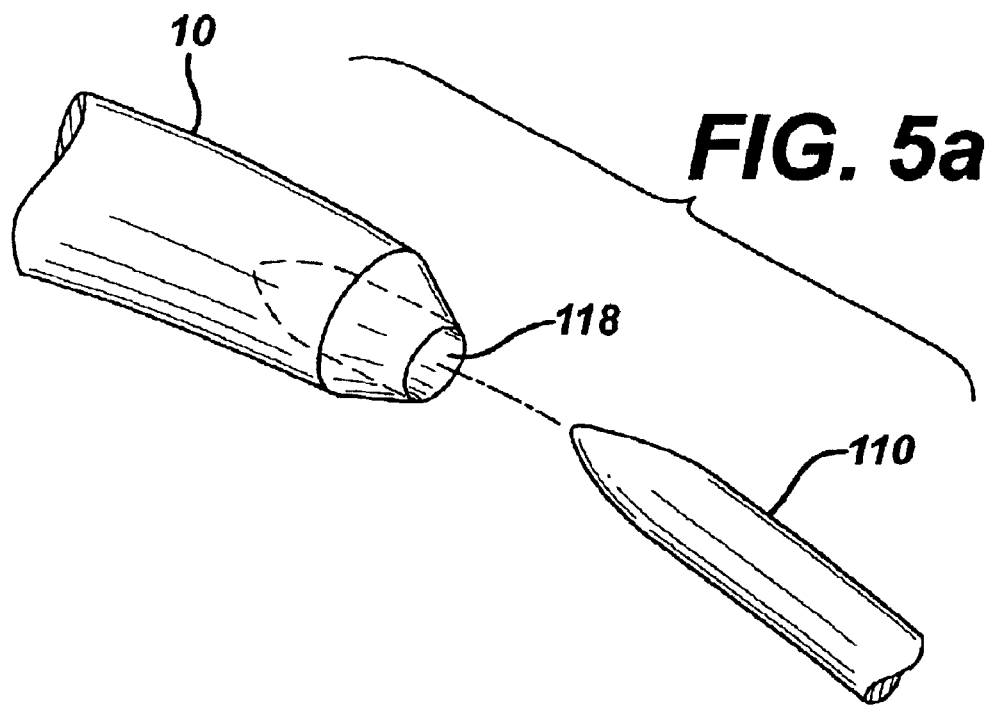
FIGS. 5a–d illustrate alternate embodiments of coupling the guide needle to the needle.
Figure 5B:
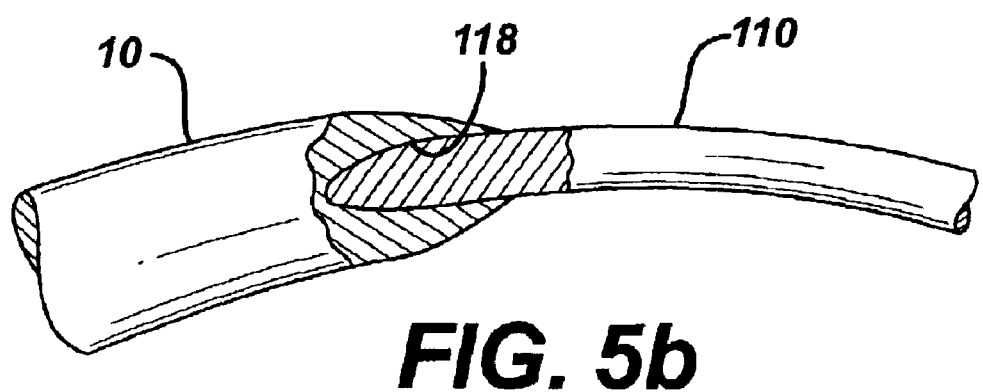

FIGS. 5a–d illustrate alternate embodiments for coupling needle 10 to guide needle 110 to implant a mesh 12 trans-abdominally as indicated above. In FIGS. 5a–b, the distal end of needle 10 is modified to include a bore opening 118 to allow for a press fit connection with the distal end of guide needle 110. Alternatively, bore-opening 118 may comprise other connection means, such as glue or a high-friction material.

Figure 5C:
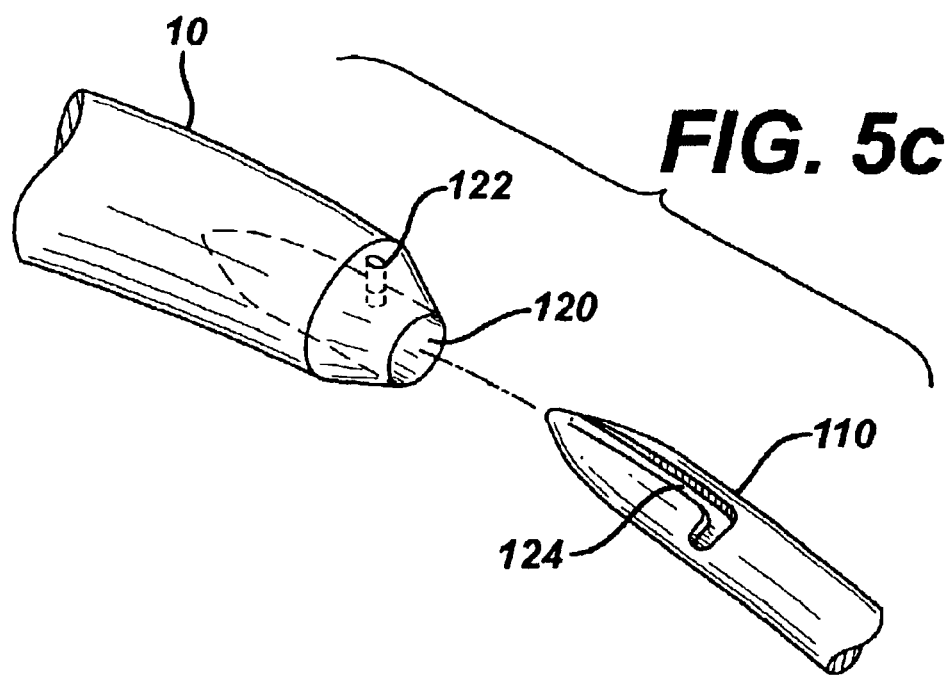
Figure 5D:
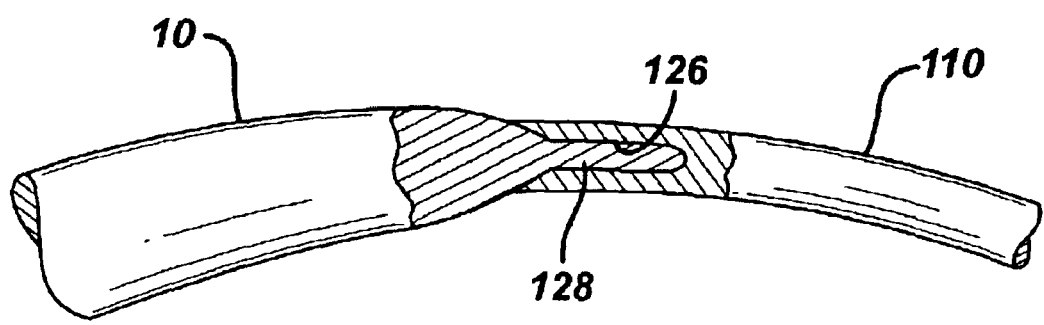

In FIG. 5c, the distal end 17 of needle 10 is modified to include a bore opening 120 and a locking pin 122. Guide needle 110 is modified to include an L-shaped groove 124. The distal end of guide needle 110 inserts into opening 120 and groove 124 engages locking pin 122 and locks thereto with a quarter-turn twist. FIG. 5d illustrates a bore opening 126 in guide needle 110 to accept a protruding element 128 at the distal end 17 of needle 10. Protruding element 128 press fits into bore opening 126.

One advantage of the embodiment shown in FIG. 3 is that the needle 10 can be used for either a trans-abdominal approach or a trans-vaginal approach. In this approach, a kit comprising two needles 10, attached to a mesh 12, at least one coupler and at least one guide needle may be distributed for use by multiple surgeon specialists. For example, a gynecologist may prefer the trans-vaginal approach and will simply discard the connector and guide needle from the kit. On the other hand, a urologist may prefer the trans-abdominal approach and utilize the connector(s) and guide needle(s).

Referring now to FIGS. 6a–h, an alternate embodiment of the invention utilizes the needle 10 to penetrate the abdominal wall 60 and couple to the mesh 12. In this embodiment, the mesh 12 is modified to create a connection means for connecting to the distal end of the needle 10. The connection means is preferably detachable so that when the mesh is pulled out of the abdominal wall, the mesh may be detached from the needle and the needle reused to retrieve the other end of the mesh. This embodiment allows for the use of a single needle for the procedure. This embodiment also allows for the use of a mesh constructed, at least in part, of natural materials, which are otherwise not suitable in the pre-affixed embodiment due to the inability of the natural material to survive extended periods in inventory.

Figure 6A:
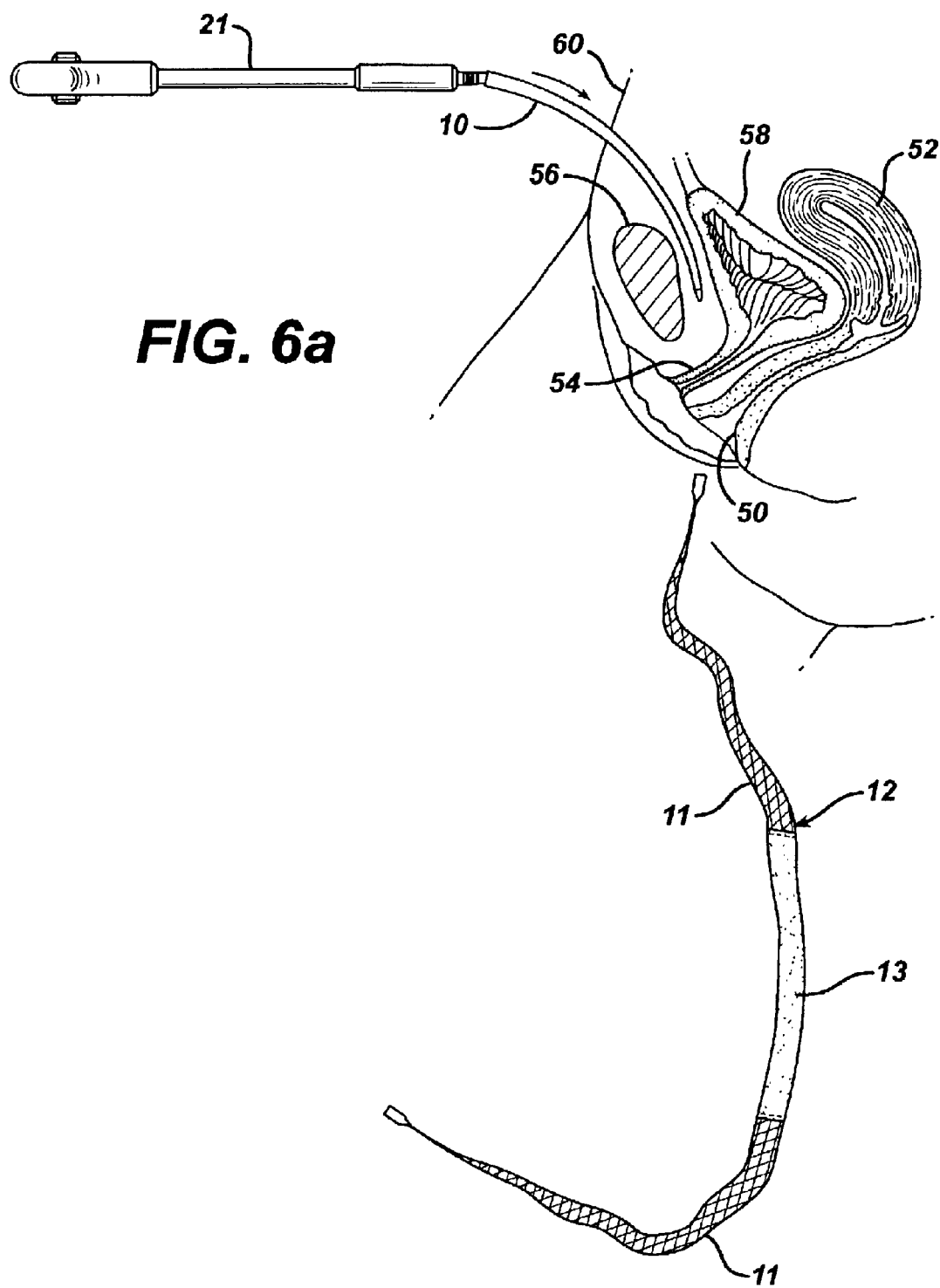
FIGS. 6a–h diagrammatically illustrate several surgical steps of a trans-abdominal method utilizing a single needle according to an alternate embodiment of the invention to treat SUI.
Figure 6B:
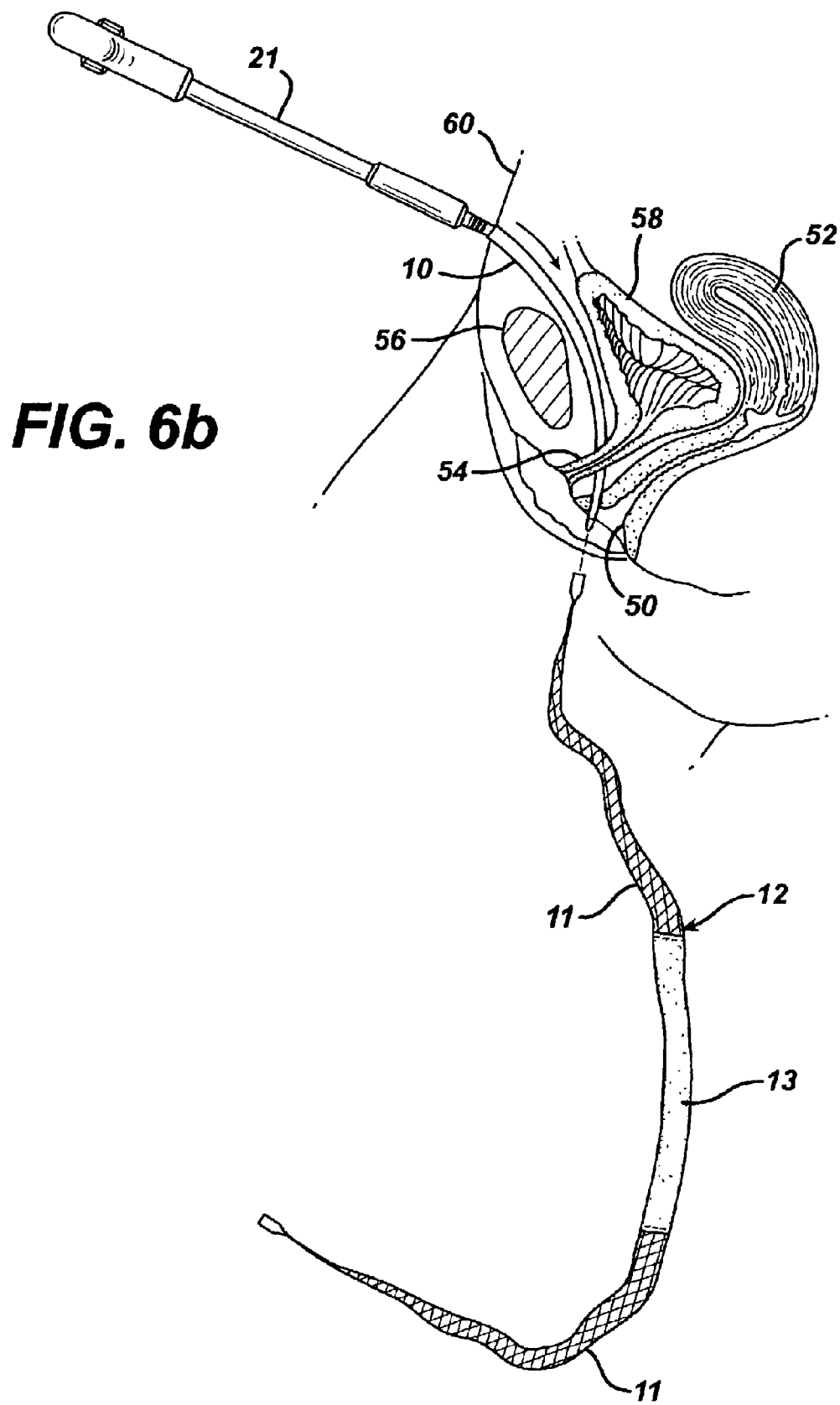
Figure 6C:
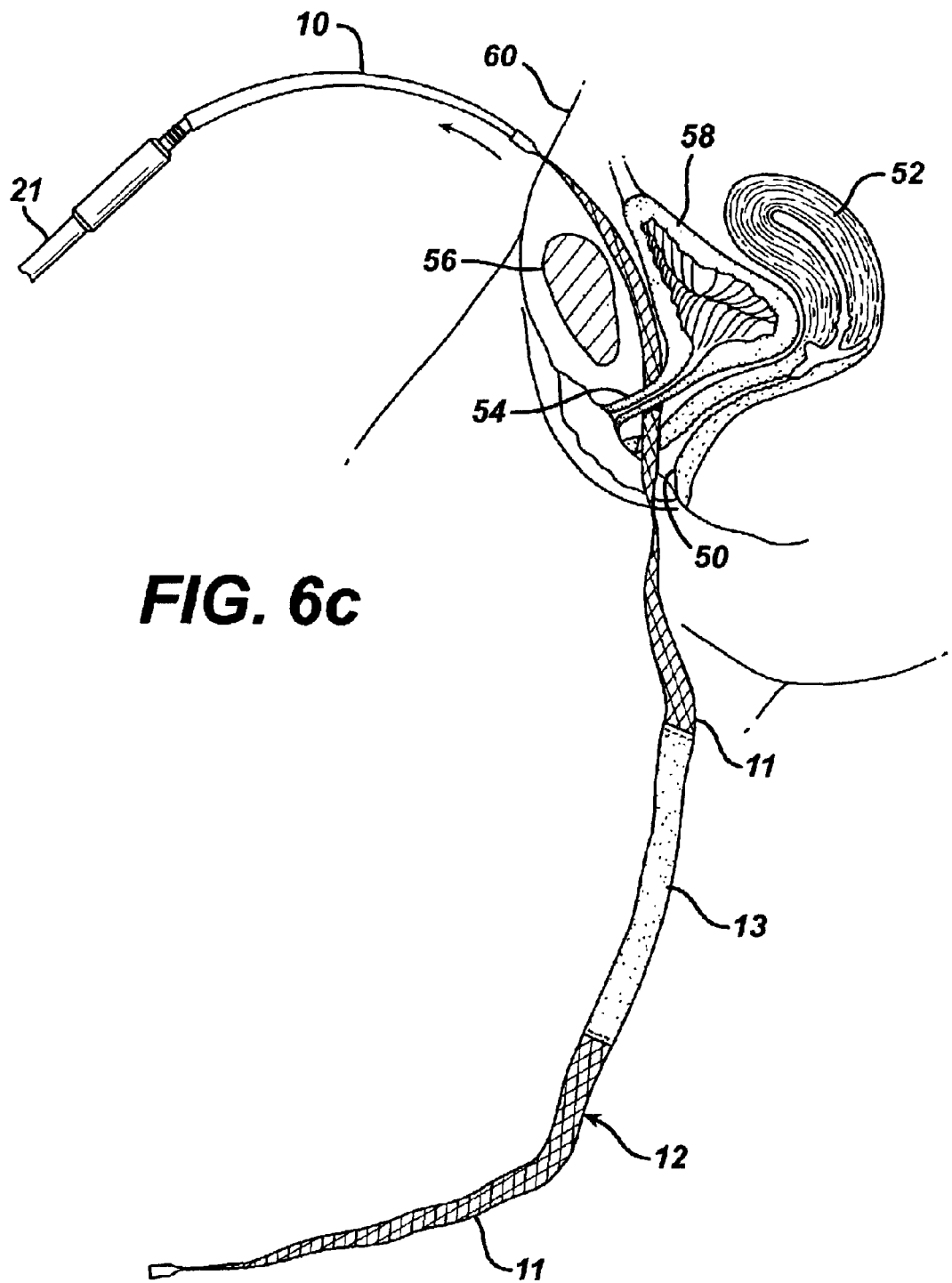
Figure 6D:
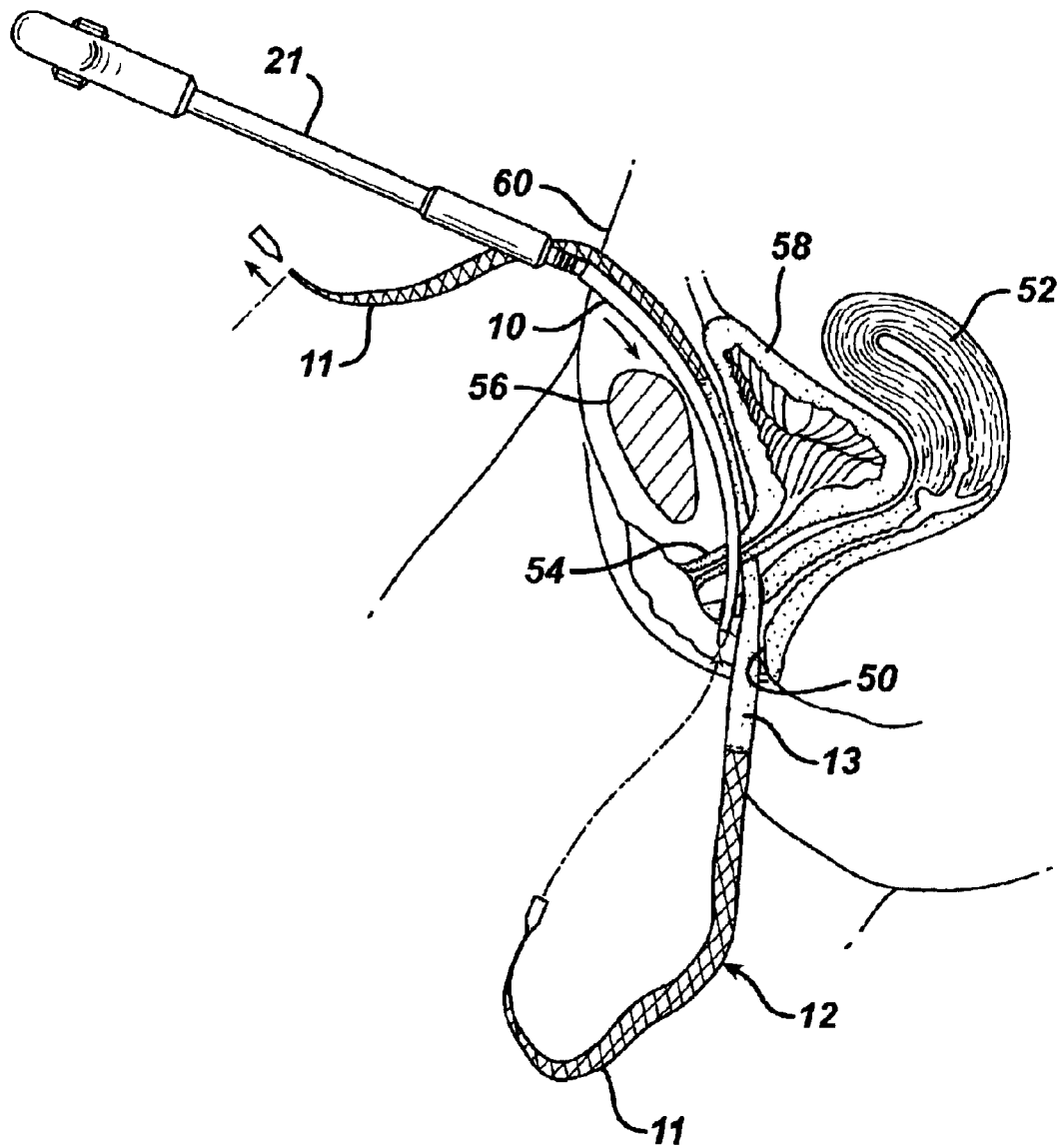
Figure 6E:
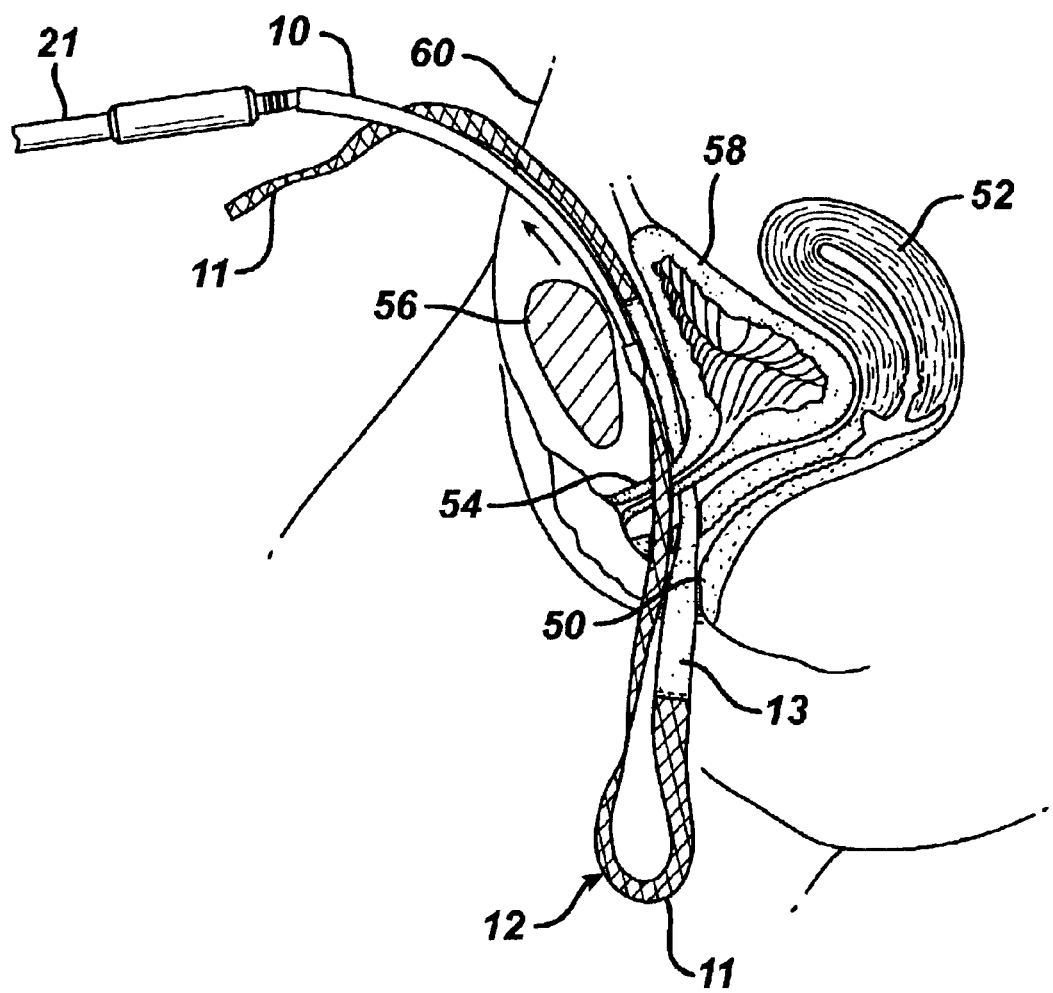
Figure 6F:
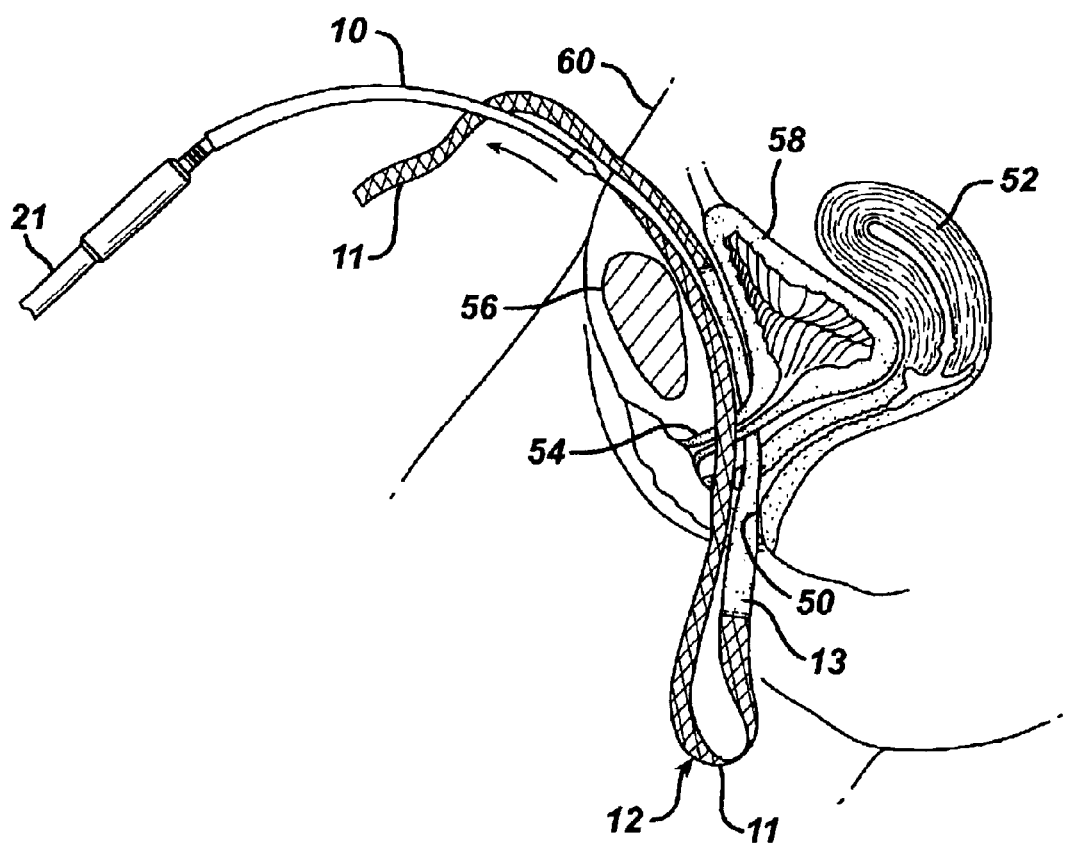
Figure 6G:
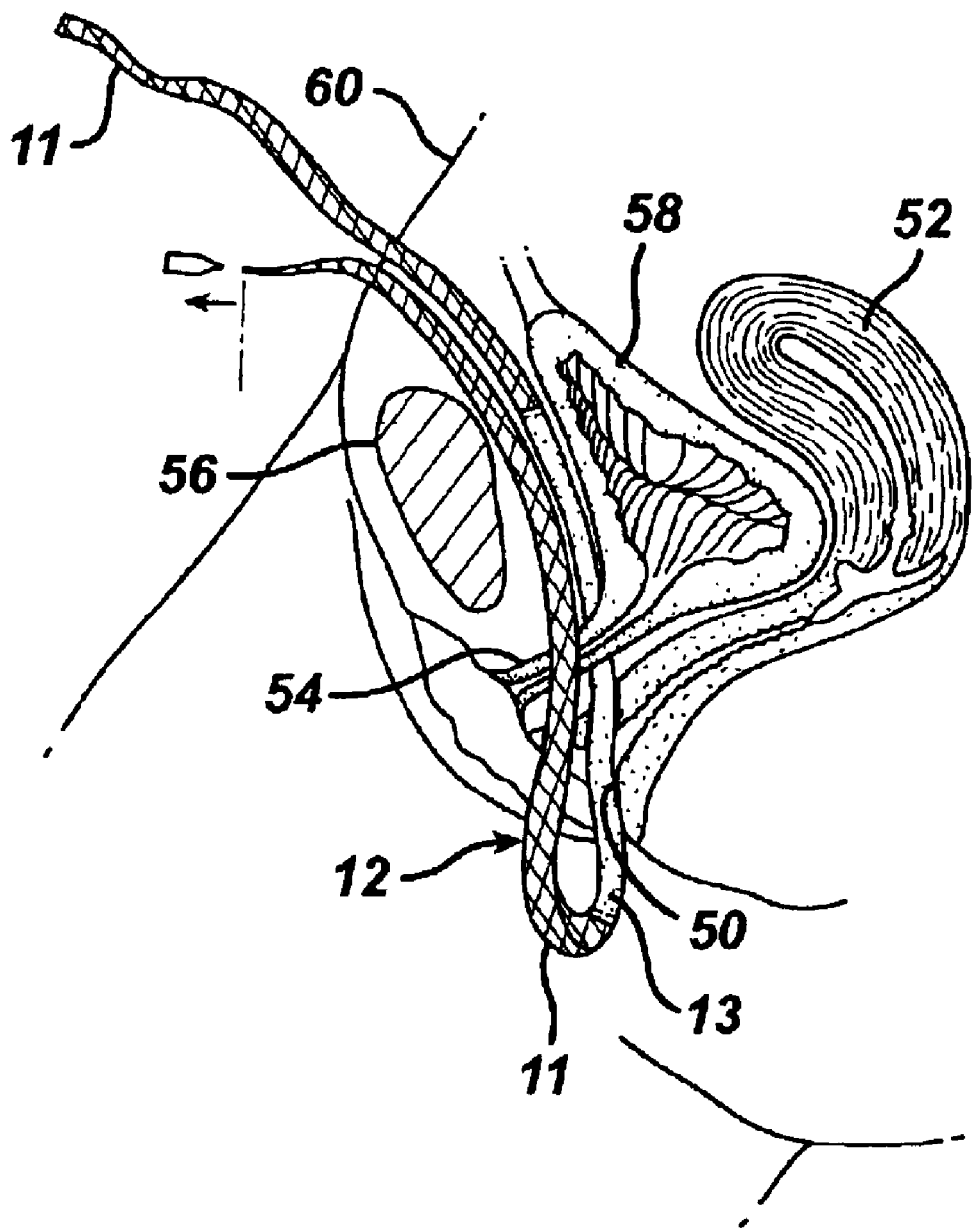
Figure 6H:
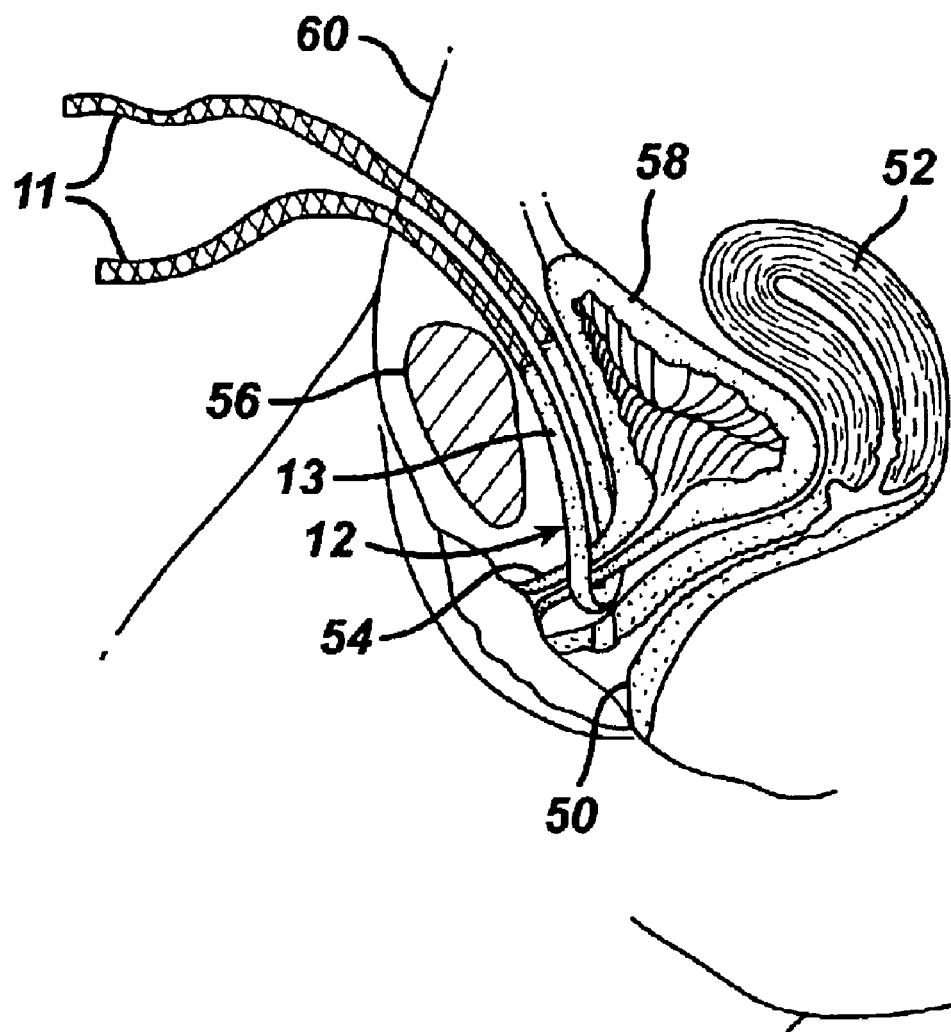

A needle 10 with coupling means at the distal end penetrates the abdominal wall 60, anterior to the pubic bone 56, FIG. 6a and follows the contour of the pubic bone 56 to one side of the urethra 54 and exits the body through an incision having been made in the anterior wall of the vagina 50, FIG. 6b. A first end of mesh 12 attaches to the distal end of needle 10 via coupling means. The surgeon then retracts needle 10 back through the pelvic cavity, following the same path created by needle 10, while at the same time causing mesh 12 to follow the needle, FIG. 4c. The needle 10 and mesh 12 pass through the vaginal wall and through the soft tissue on one side of the urethra 54. The needle and mesh then according to FIG. 4f being passed close to the back of the pubic bone 56, through additional layers of fat, muscle and fascia, and then out the abdominal wall 60 above the pubic bone 56.

Needle 10 disconnects from the first mesh end, and the surgeon repeats the same procedure, but this time passes the needle 10 on the opposite side of the urethra 54, FIGS. 6d–h, to complete the implantation of the mesh 12 between the mid urethra and vaginal wall.

Figure 7A:
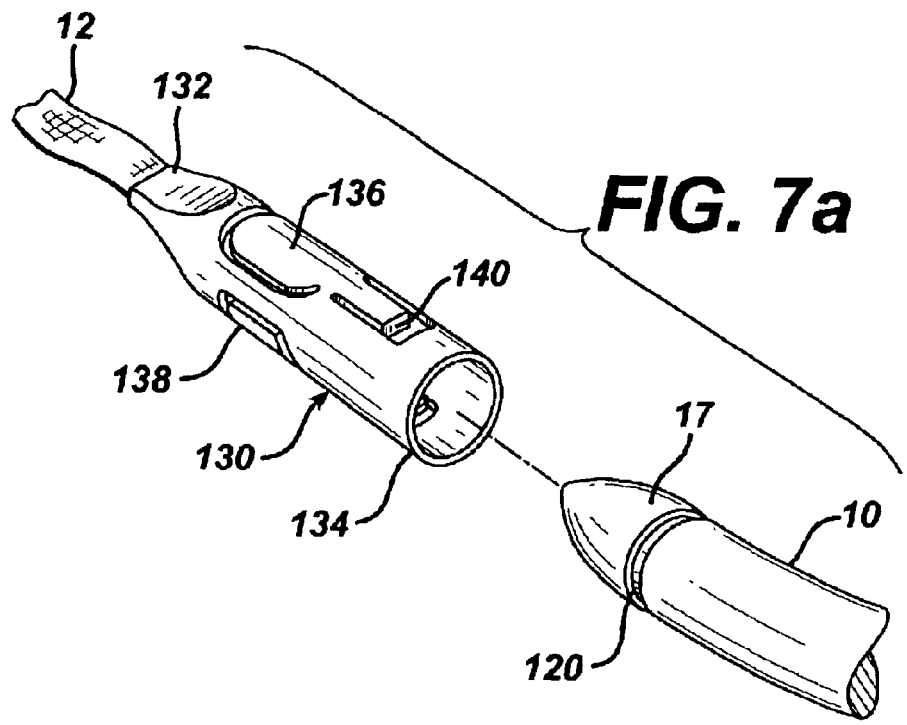
FIGS. 7a–g illustrate alternate embodiments of coupling the needle to the mesh.
Figure 7B:
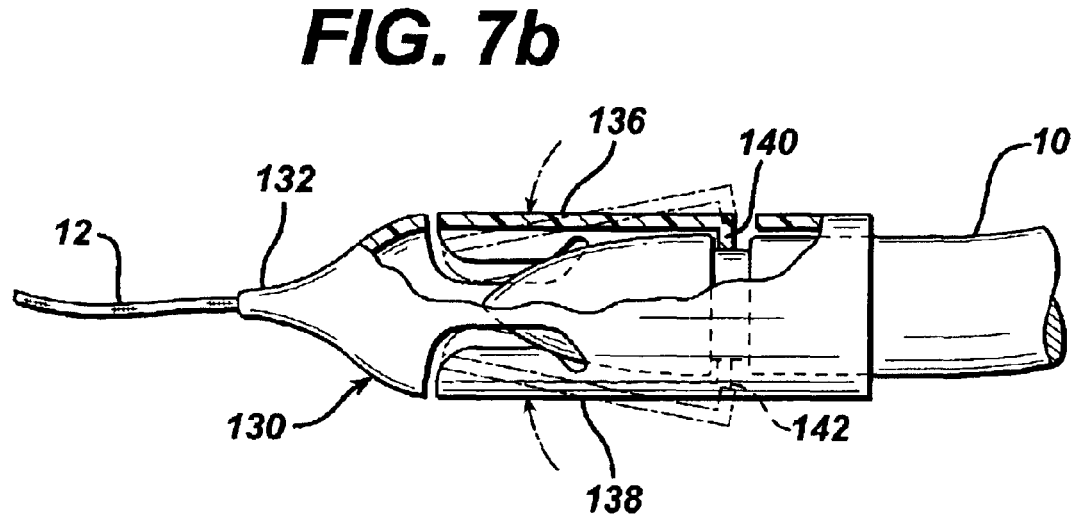

Referring to FIGS. 7a–g, alternate embodiments for connecting the needle 10 to the mesh 12 are disclosed. FIGS. 7a–b disclose a coupler 130 having a proximal end 132 configured to accept the mesh 12 and a distal end 134 for accepting the distal end 17 of needle 10. Distal end 17 comprises a contiguous groove 120 for detachably coupling with coupler 130. Coupler 130 further comprises two spring tabs 136 and 138, each with fingers 140 and 142 for engaging groove 120. Mesh 12 is preferably attached to the distal end 132 using a biocompatible glue or other appropriate mechanical fastening means. The surgeon may simply attach or detach needle 10 from coupler 130 by depressing spring tabs 136 and 138 forcing fingers 140 and 142 upward to allow distal end 17 to slide in or out of coupler 130. Fingers 140 and 142 engage groove 120 to hold needle 10 firmly in place within coupler 130.

Figure 7C:
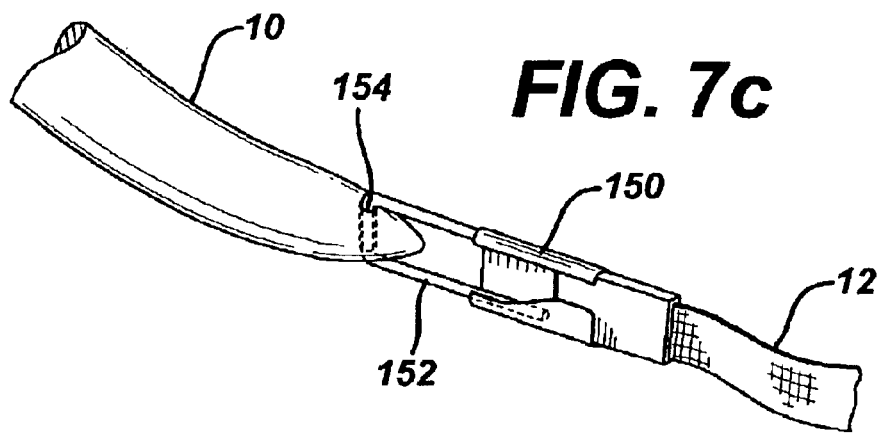
Figure 7D:
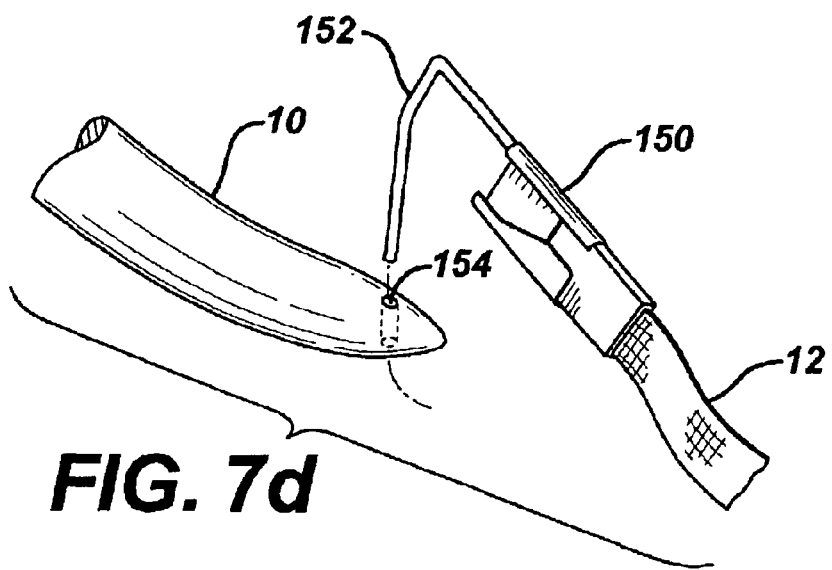
Figure 7E:
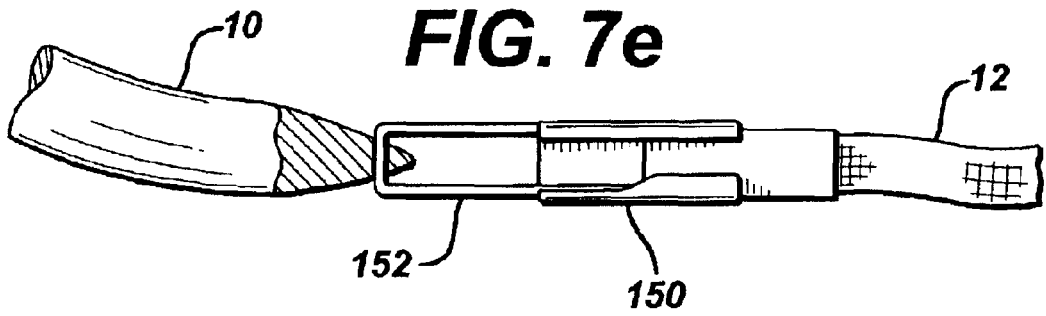

FIGS. 7c–e illustrate a coupling mechanism 150 similar in function to a safety pin. Spring arm 152 engages with a bore 154 at the distal end 17 of needle 10.

Figure 7F:
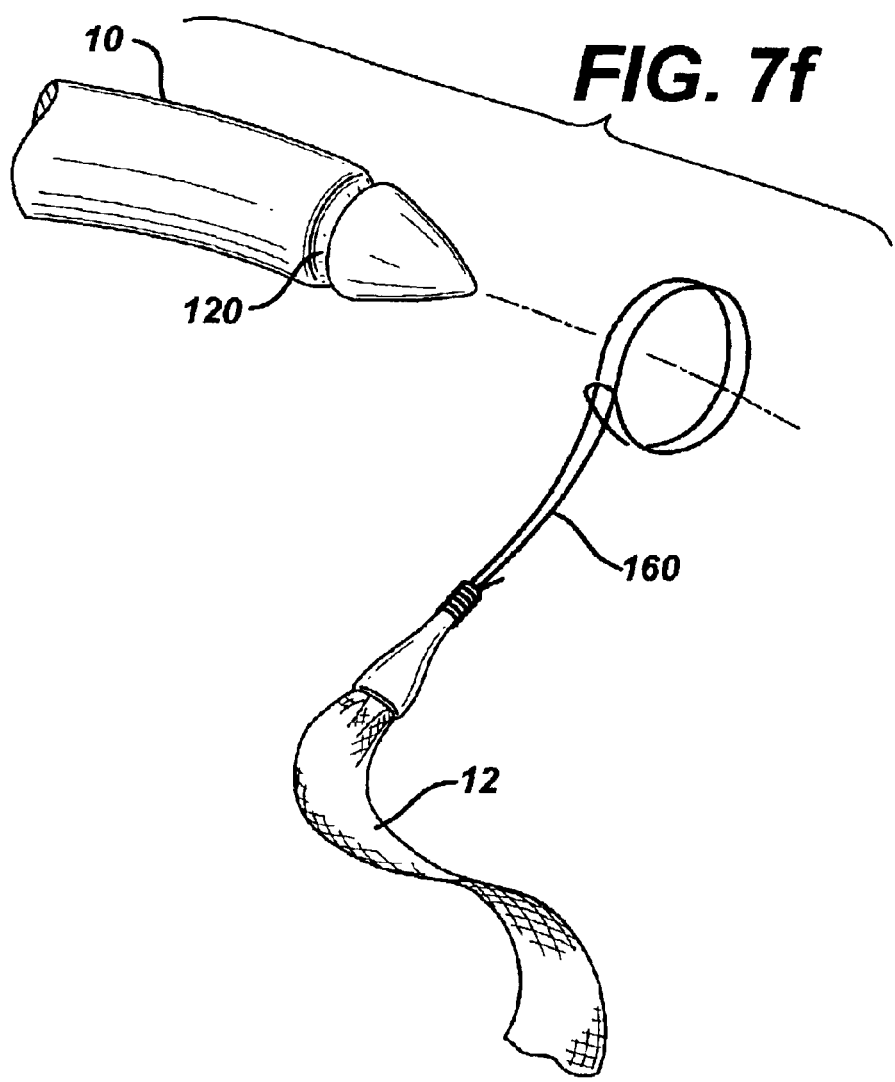
Figure 7G:
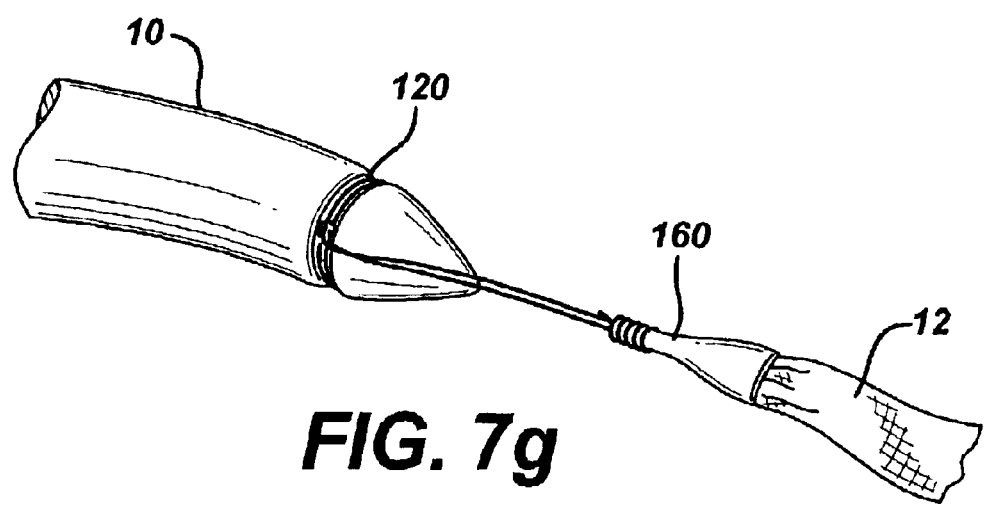

FIGS. 7f–g illustrate a loop coupling mechanism 160 attached to mesh 12 for engaging groove 120.

As would be appreciated by one skilled in the art, there exist multiple means for detachably connecting the mesh to the needle.

Another alternate embodiment of the present invention for trans-abdominally implanting mesh 12 while the patient is under local anesthesia only is shown in FIGS. 9a–9k. Similar to the embodiment shown in FIGS. 8a–8i, the alternate embodiment shown in FIGS. 9a–9k utilizes two needles and a guide needle. In this embodiment, however, the guide needle is specifically an anesthesia needle 110a capable of delivering local anesthesia, which is carried therein, to the patient. The anesthesia needle 110a has an outer diameter that is smaller than the outer diameter of each of the needles 10a, 10b and, more particularly, is preferably about 2 mm.

Figure 9A:
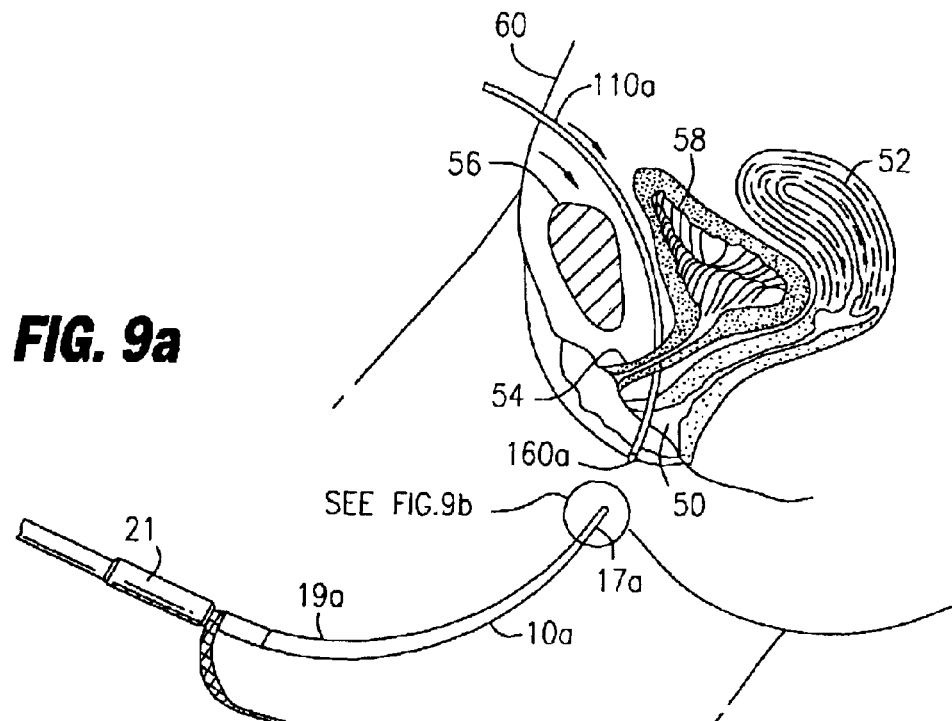
FIGS. 9a–k diagrammatically illustrate several surgical steps of a trans-abdominal method utilizing two needles and an anesthesia needle according to another alternative embodiment of the invention to treat SUI performed with local anesthesia only.
Figure 9B:
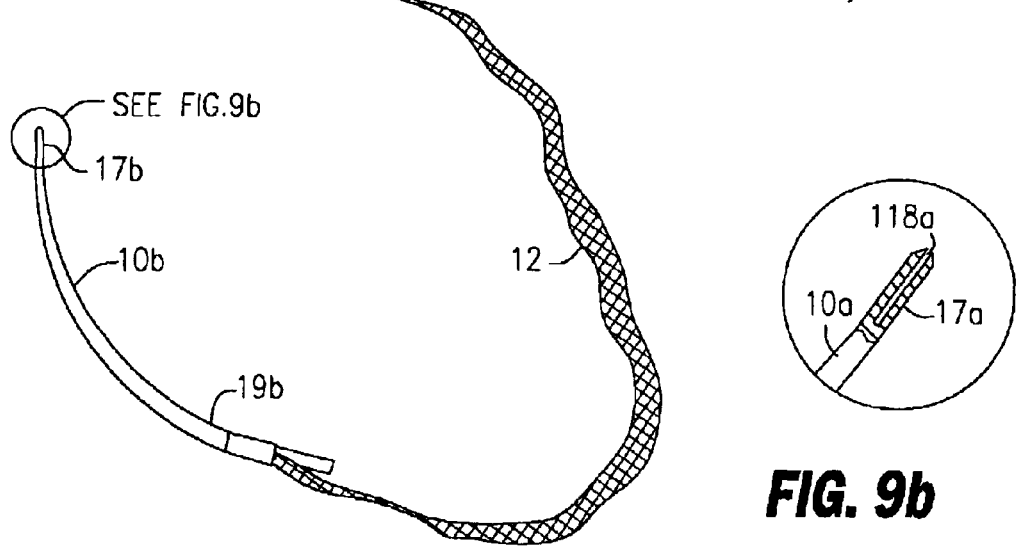
Figures 9C, 9D:
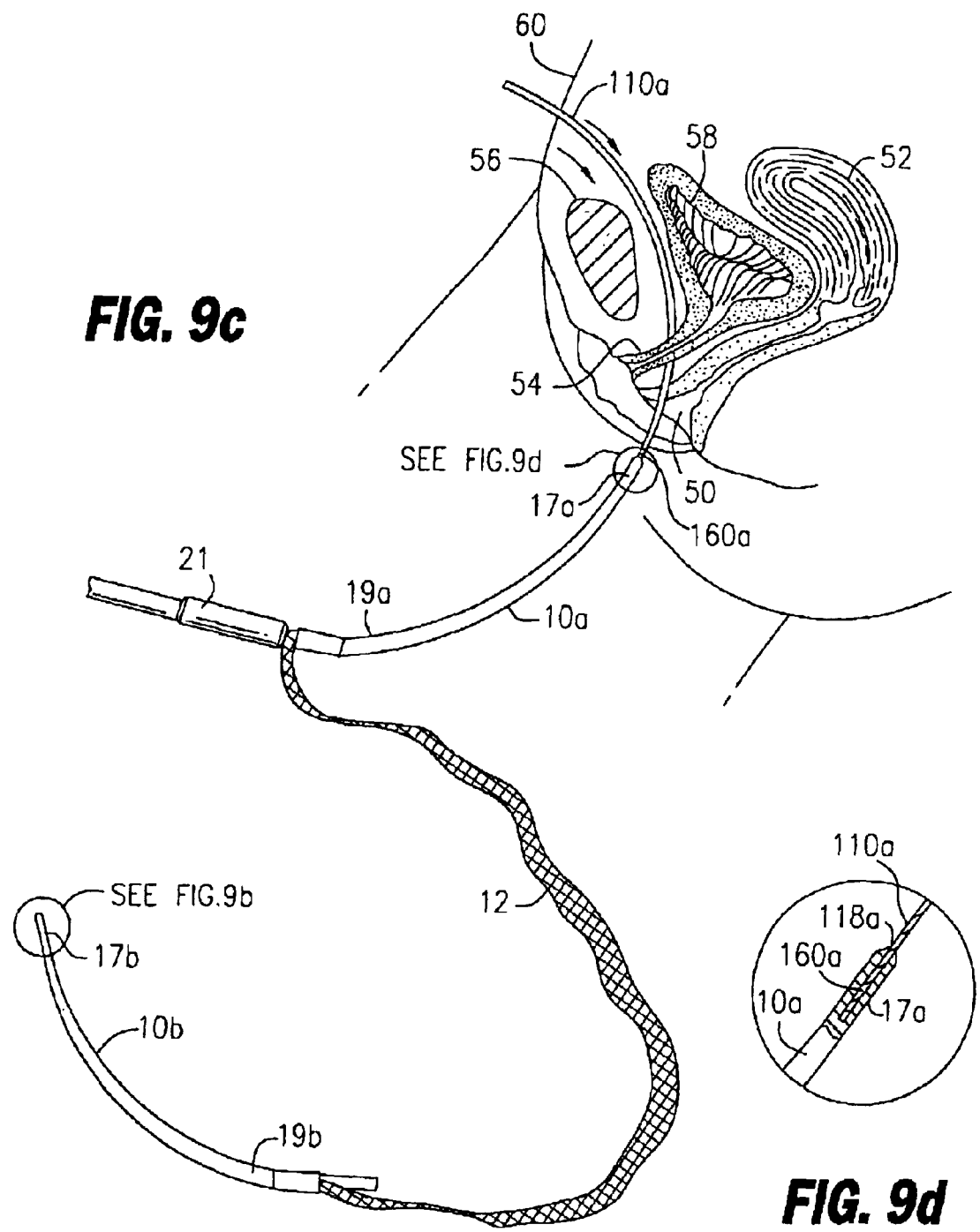
Figure 9E:
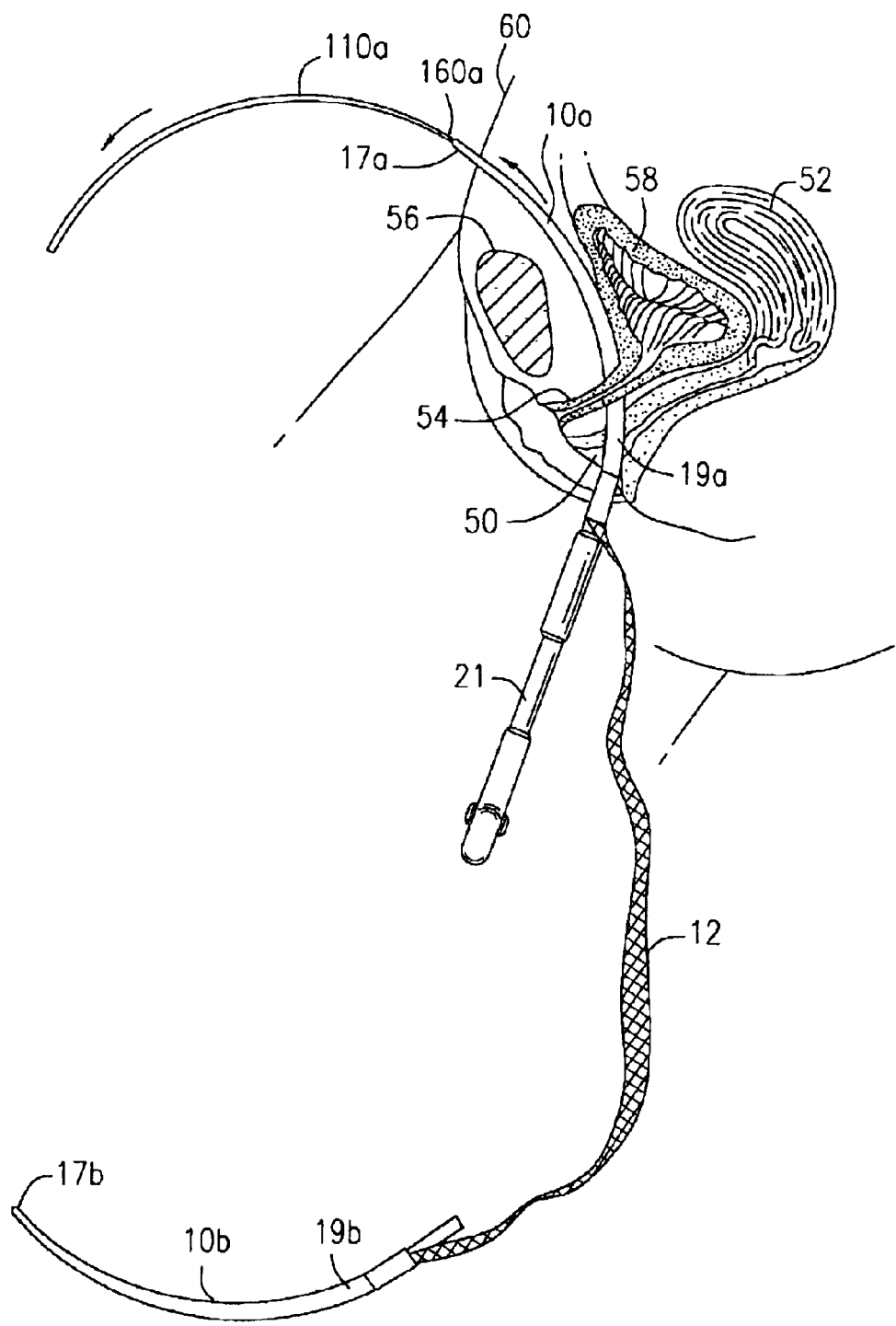
Figure 9F:
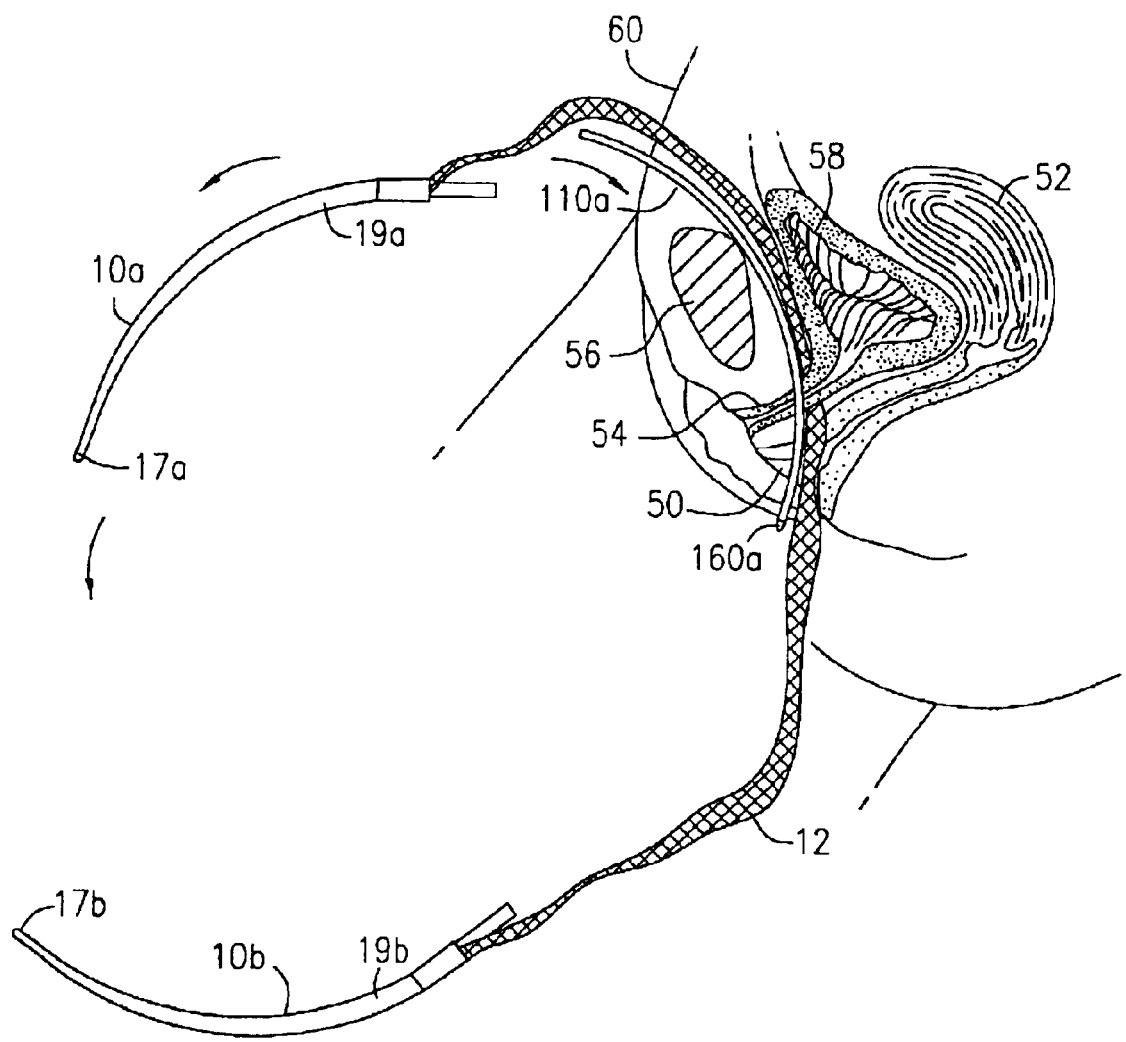
Figure 9G:
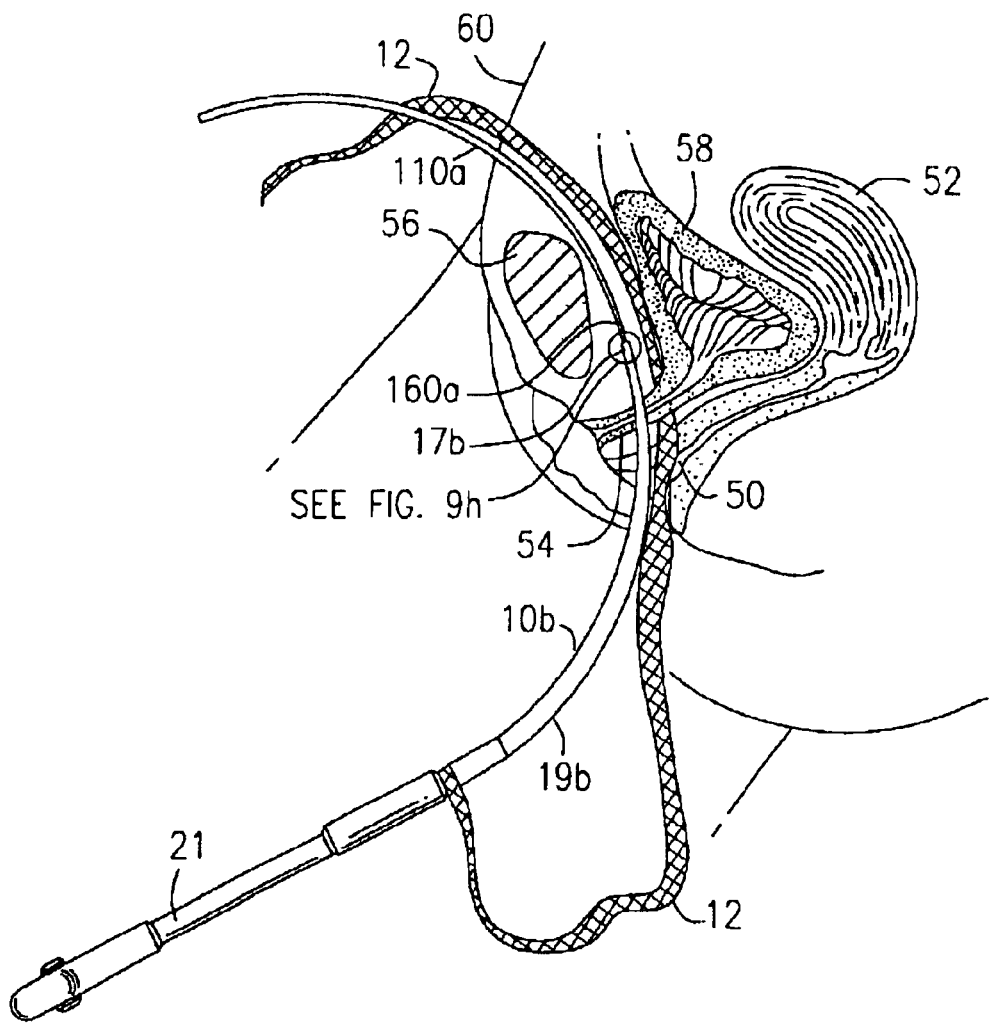
Figure 9H:
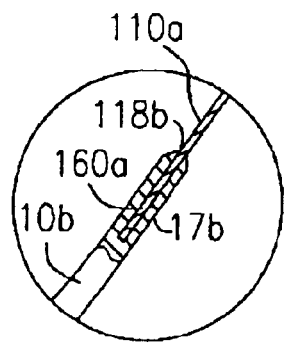
Figure 9I:
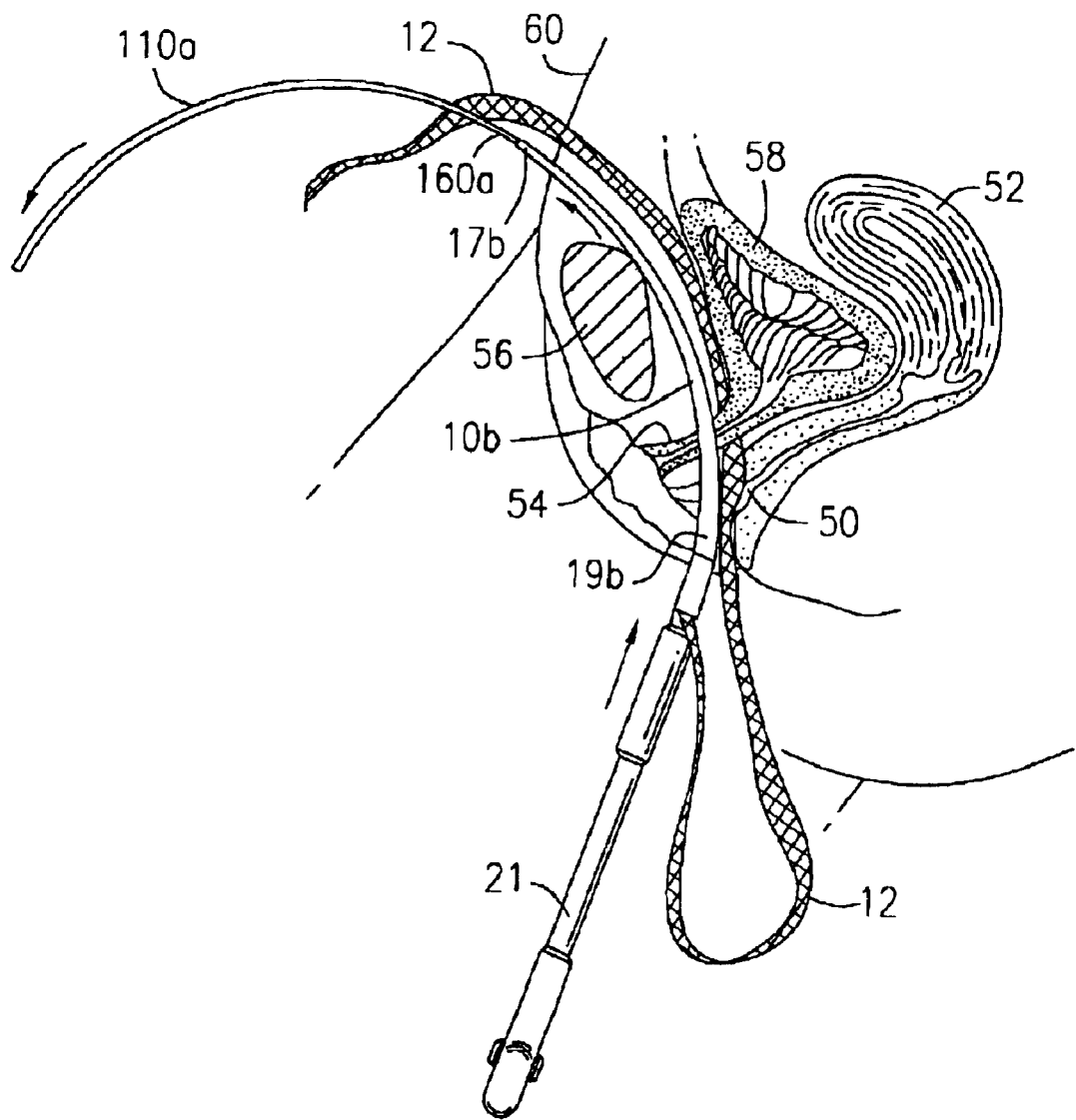
Figure 9J:
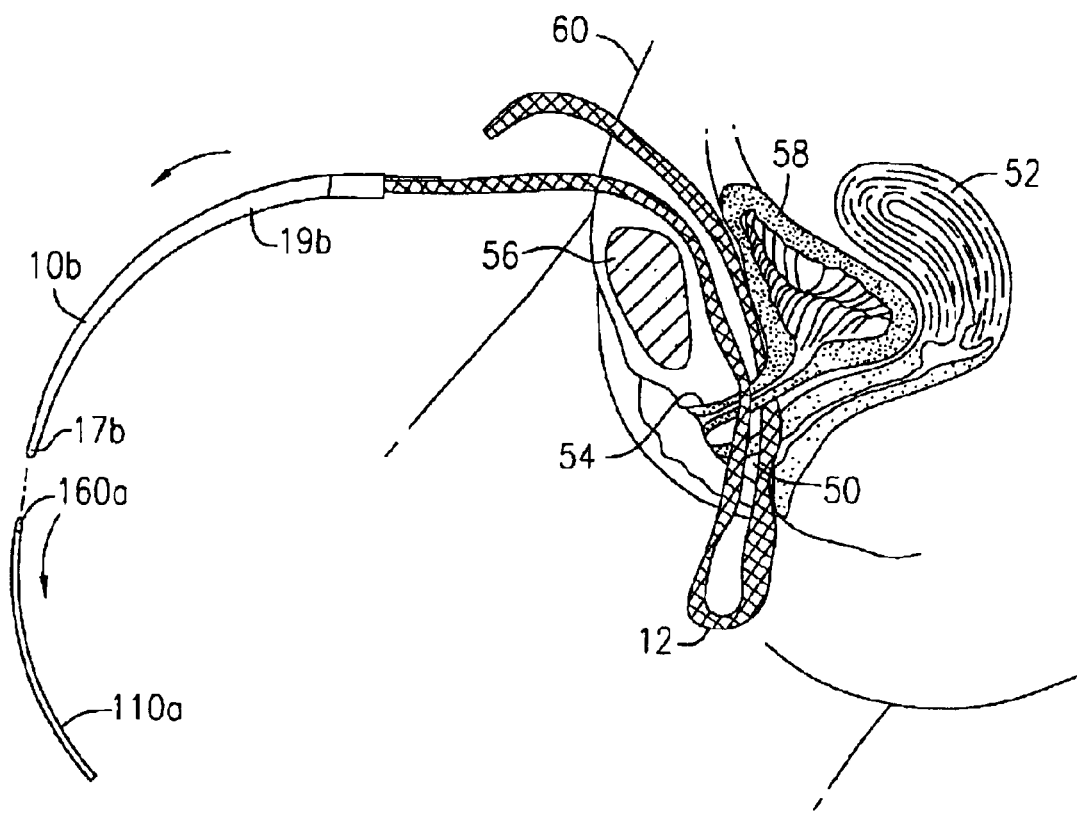
Figure 9K:
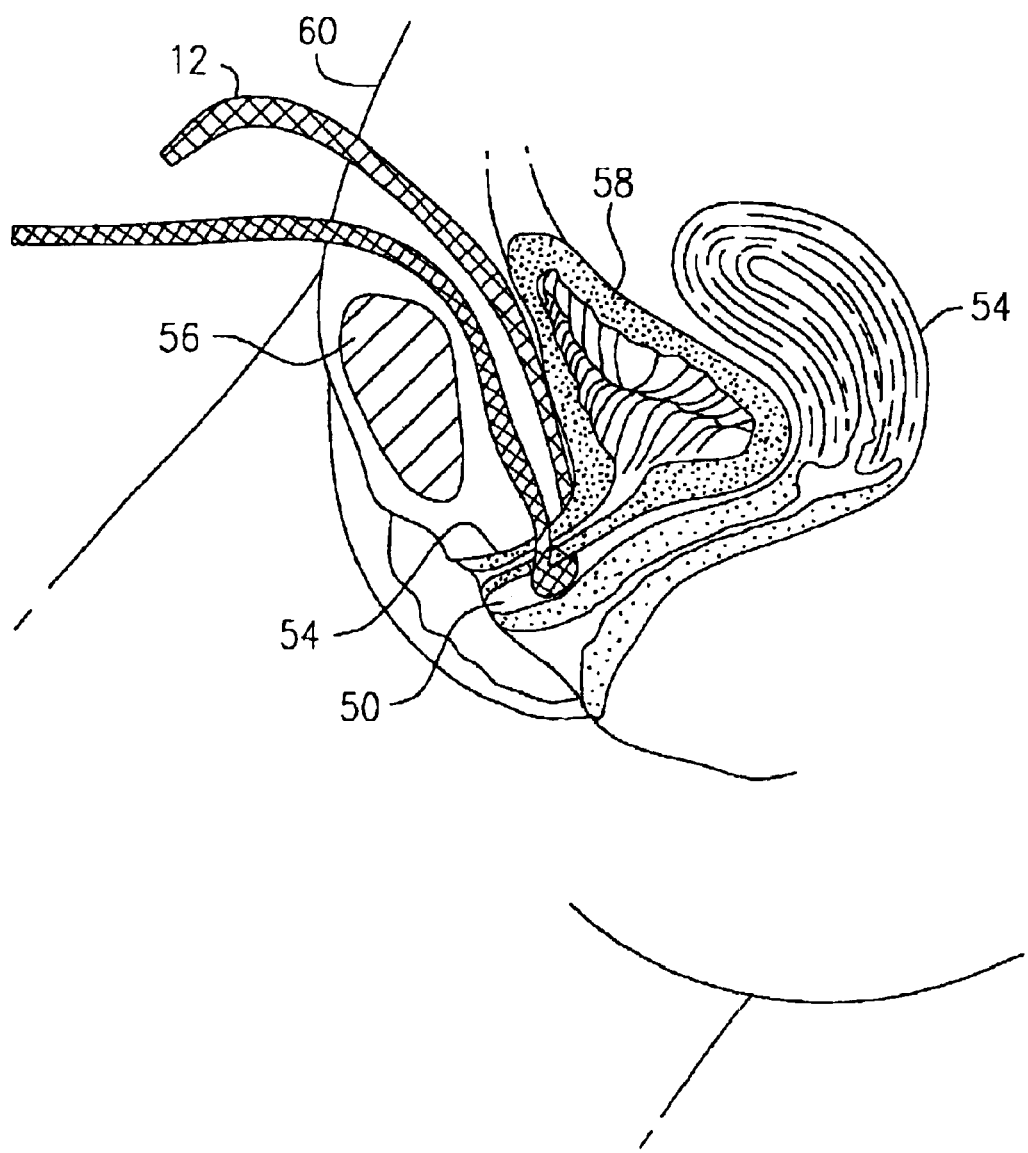

As shown in FIGS. 9b, 9d and 9h, in particular, the distal ends 17a, 17b, 160a of the needles 10a, 10b and the anesthesia needle 110a, respectively, are adapted to connect with one another in a manner similar to that shown in FIGS. 5a and 5b. More particularly, the distal end 17a, 17b of each of the needles 10a, 10b has a bore opening 118a, 118b, respectively, that is sized and shaped for frictionally receiving the distal end 160a of the anesthesia needle 110a. The distal end 160a of the anesthesia needle 110a can be retained within the respective bore openings 118a, 118b by other means, including but not limited to, glue, ribbing, threading, or use of a high-friction material.

In addition, the needles 10a, 10b and the anesthesia needle 110a could have other configurations, as discussed hereinabove, that facilitate connecting their distal ends together during the implantation procedure, such as including a separate connector element (see FIGS. 3a–3d) or adapting the distal ends 17a, 17b of the needles 10a, 10b to each include a bore opening and a locking pin and adapting the distal end 160a of the anesthesia needle 110a to include an L-shaped groove (not shown, but see FIG. 5c).

In accordance with this alternative procedure, the anesthesia needle 110a, with local anesthesia carried therein for injection into the patient, penetrates the abdominal wall 60, anterior to the pubic bone 56 and follows the contour of the pubic bone 56 to one side of the urethra 54 and exits the body through an incision having been made in the anterior wall of the vagina 50. At various positions along the aforesaid pathway through the patient's abdomen, the anesthesia needle 110a is paused and a clinically effective amount of local anesthetic is injected into the patient before moving the anesthesia needle 110a further along. The anesthesia needle 110a may be paused and local anesthetic injected as many times as the surgeon deems necessary, depending upon the condition of the patient and other clinical factors, with which persons having ordinary skill in the art will be familiar. The purpose of the aforesaid pauses is to anesthetize the needle pathway for a further purpose which will become clear hereinafter.

After the distal end 160a of the anesthesia needle 110a extends out of the anterior wall of the vagina 50, a first one of the two needles 10a is then attached thereto by inserting the distal end 160a of the anesthesia needle 110a into the bore opening 118a of the distal end 17a of first needle 10a (see FIG. 9c). It is noted that one end of the mesh 12 is connected to the proximal end 19a of the needle 10a in any one of the ways already described hereinabove.

The anesthesia needle 110a is then withdrawn back through the anesthetized pathway made by the anesthesia needle 110a in the patient's body, whereby the needle 10a and the tape, or mesh 12, attached thereto are also drawn through the patient's abdomen. The needles 10a, 110a pass through the anterior wall of the vagina 50 and through the soft tissue on one side of the urethra 54, the needles 10a, 110a being passed close to the back of the pubic bone 56, through additional layers of fat, muscle and fascia, and then out the abdominal wall 60 above the pubic bone 56, FIGS. 9c and 9e. It is noted that, although the diameter of the first needle 10a is significantly greater than the diameter of the anesthesia needle 110a, the fact that the pathway has already been anesthetized during the passage of the anesthesia needle 110a therethrough facilitates the retraction of the first needle 10a and mesh 12 therethrough. Next, the surgeon uncouples handle 21 from the needle 10a and pulls needle 10a out of the body through the abdominal wall 60, FIG. 9f.

The surgeon repeats the foregoing steps, using the anesthesia needle 110a and the second of the two needles 10b, whereby the needles 10b, 110a are passed on the opposite side of the urethra 54, to complete the implantation of the mesh 12 between the mid-urethra and anterior wall of the vagina 50, using needle 10b (see FIGS. 9f–j). It is noted that this second passage of the anesthesia needle 110a into and through the patient's abdomen may or may not include pauses to inject local anesthesia into the patient, depending upon whether the first passage and paused injections accomplished sufficient anesthesia of the surgical area to enable passage of the second needle 10b and mesh 12 therethrough, as determined by clinical conditions in an manner well understood by those having ordinary skill in the art.

It is further noted that the alternate procedure shown in FIGS. 9a–9k and described above may be performed using two anesthesia needles 110a, 110b (in a manner described previously in connection with FIGS. 8a–8i), rather than only one as shown in FIGS. 9a–9k. As will be readily understood by persons having ordinary skill in the art, the alternate procedure shown in FIGS. 9a–9k may also be performed using an anesthesia needle and only one needle (i.e., needle 10a) removably attached to the mesh 12, or one anesthesia needle and no needles attached to the mesh 12 (see, for example, FIGS. 6a–6f).

Since all procedures may be performed using a local anesthesia, rather than general anesthesia, they can be performed as outpatient procedures in the surgeon's office or another outpatient facility, rather than requiring admission to a hospital. Additionally, the patient is able to provide feedback to the surgeon during the procedure, after the mesh 12 is in place. Typically, the urinary bladder 58 is filled with a fluid, such as water, using a catheter and the patient is requested to cough. The surgeon is able to determine the operation of the urethra and may adjust the placement of the mesh 12, as necessary, by adjusting the ends of mesh 12 located at the outside of the abdomen 60, FIGS. 4h and 5h. After adjustments, the surplus mesh at the abdomen is cut off, and the ends of the mesh are secured within the abdomen and the abdomen is closed. Likewise, the incision at the vaginal wall is closed whereby the tissue flap seals the mesh between the urethra 54 and the wall of vagina 50.

Mesh 12 is left in the body and forms an artificial ligament attached to the abdominal wall that provides the support for the urethra as required in order to restore urinary continence to the patient.

Figure 4A:
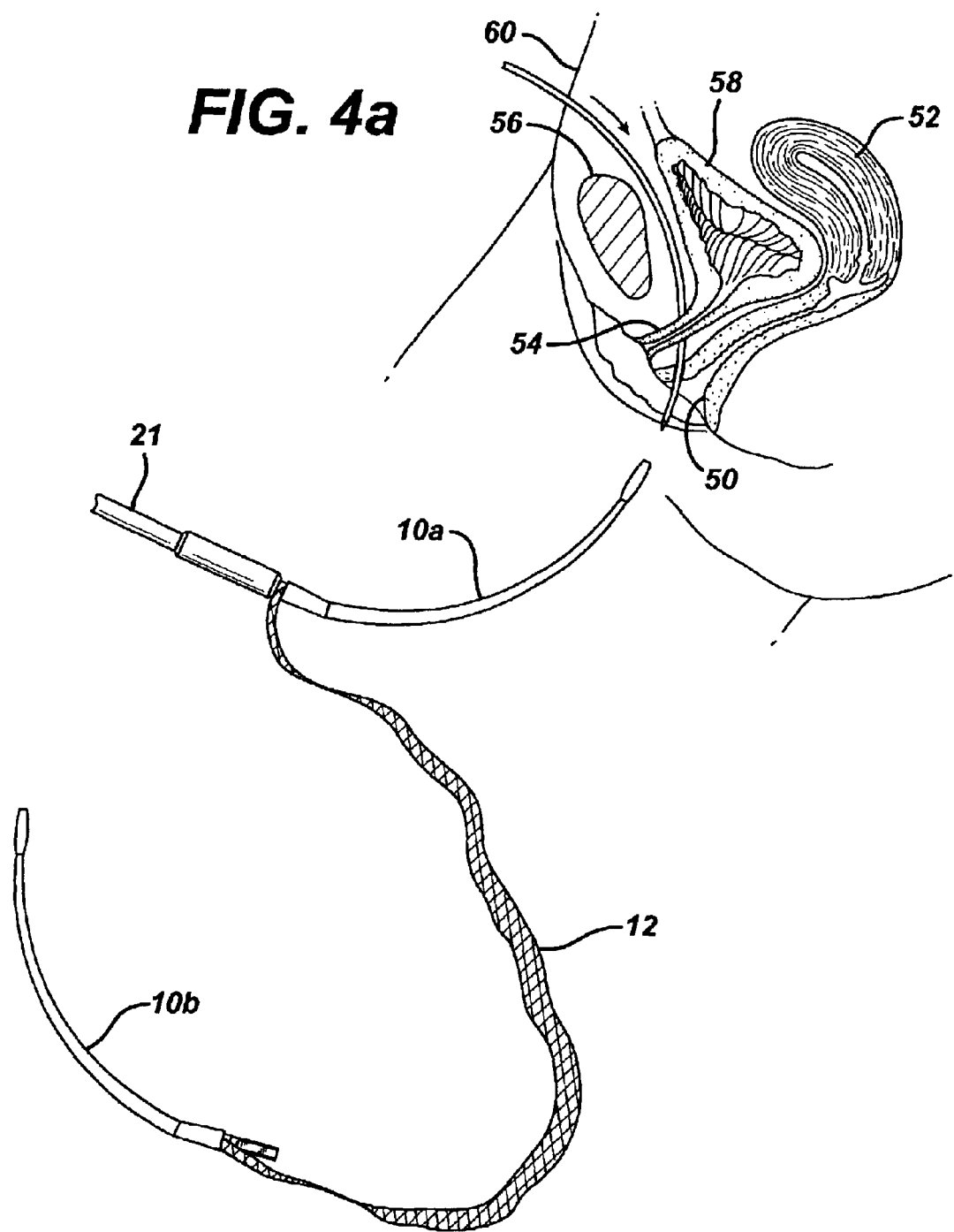
FIGS. 4a–j diagrammatically illustrate several surgical steps of a trans-abdominal method utilizing two needles and guide needle according to the invention to treat SUI.
Figure 4B:
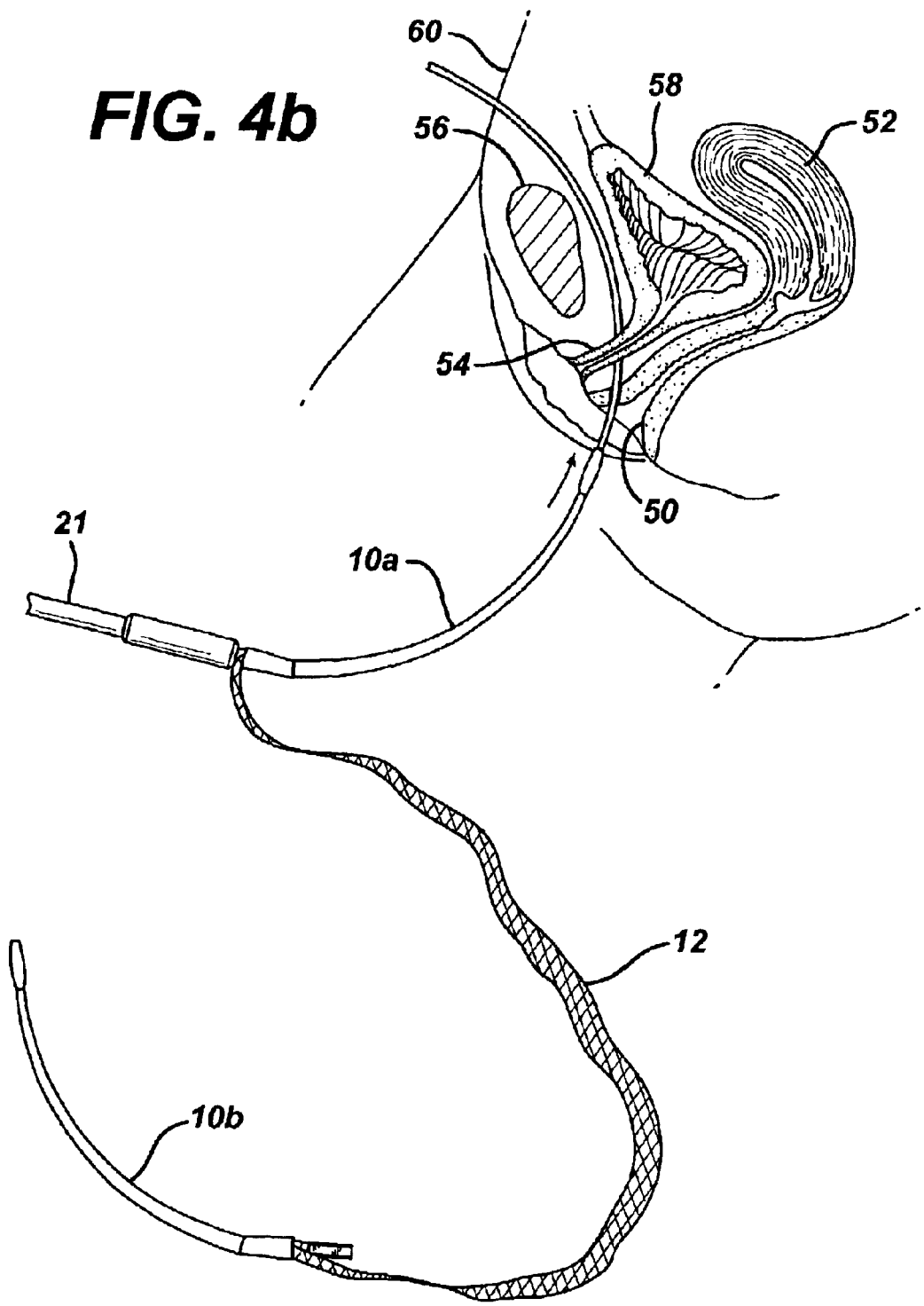
Figure 4C:
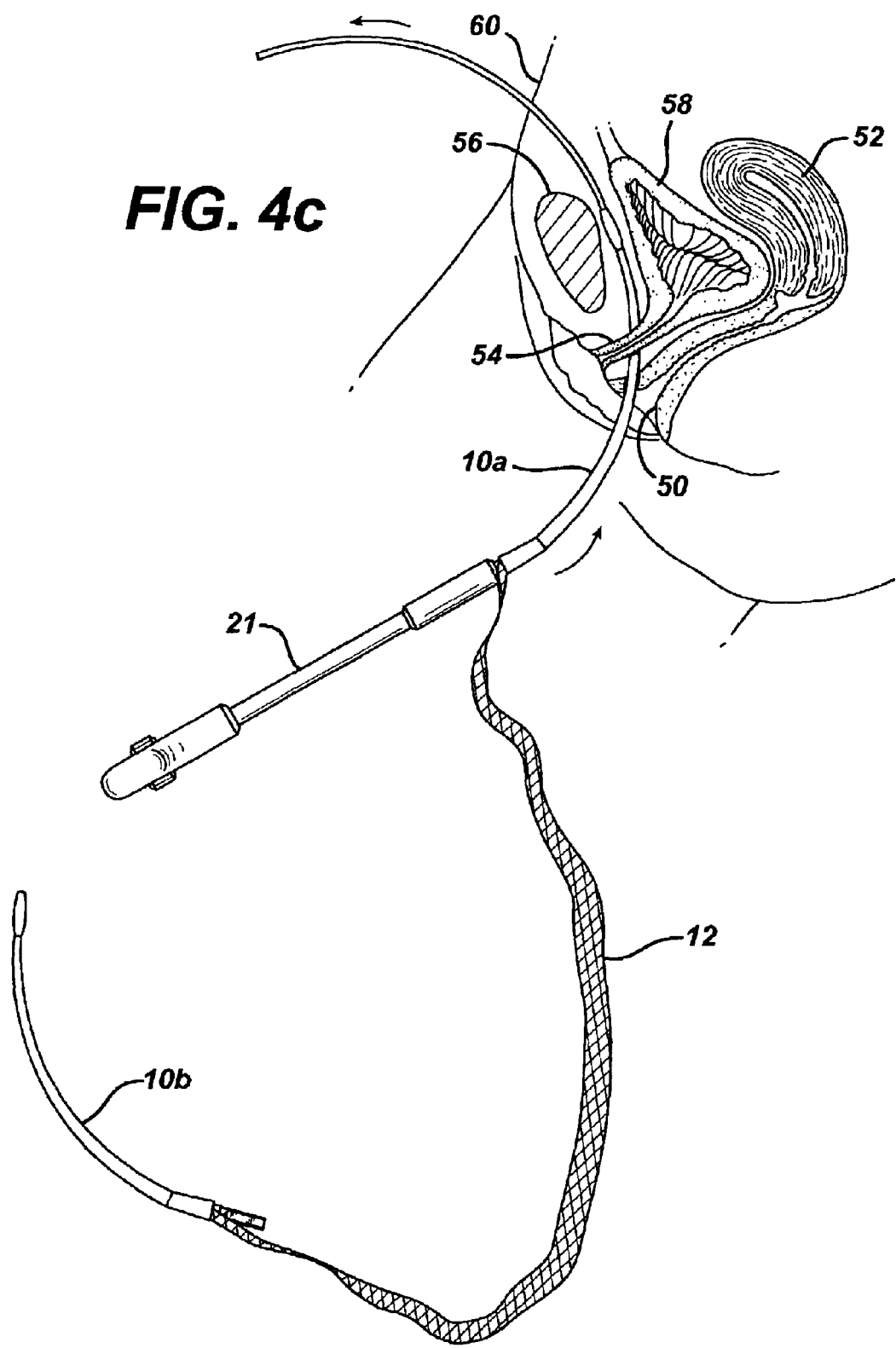
Figure 4D:
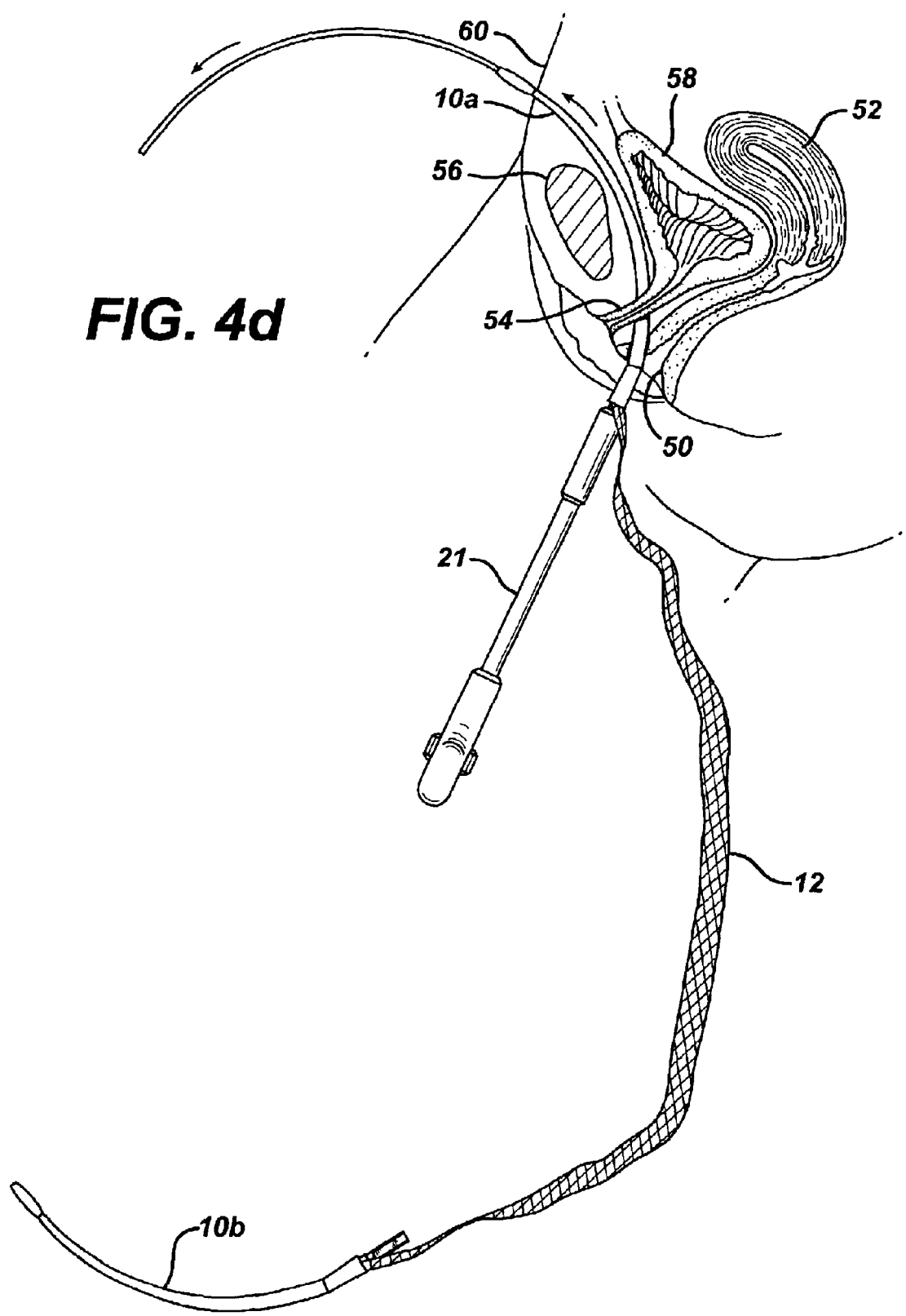
Figure 4E:
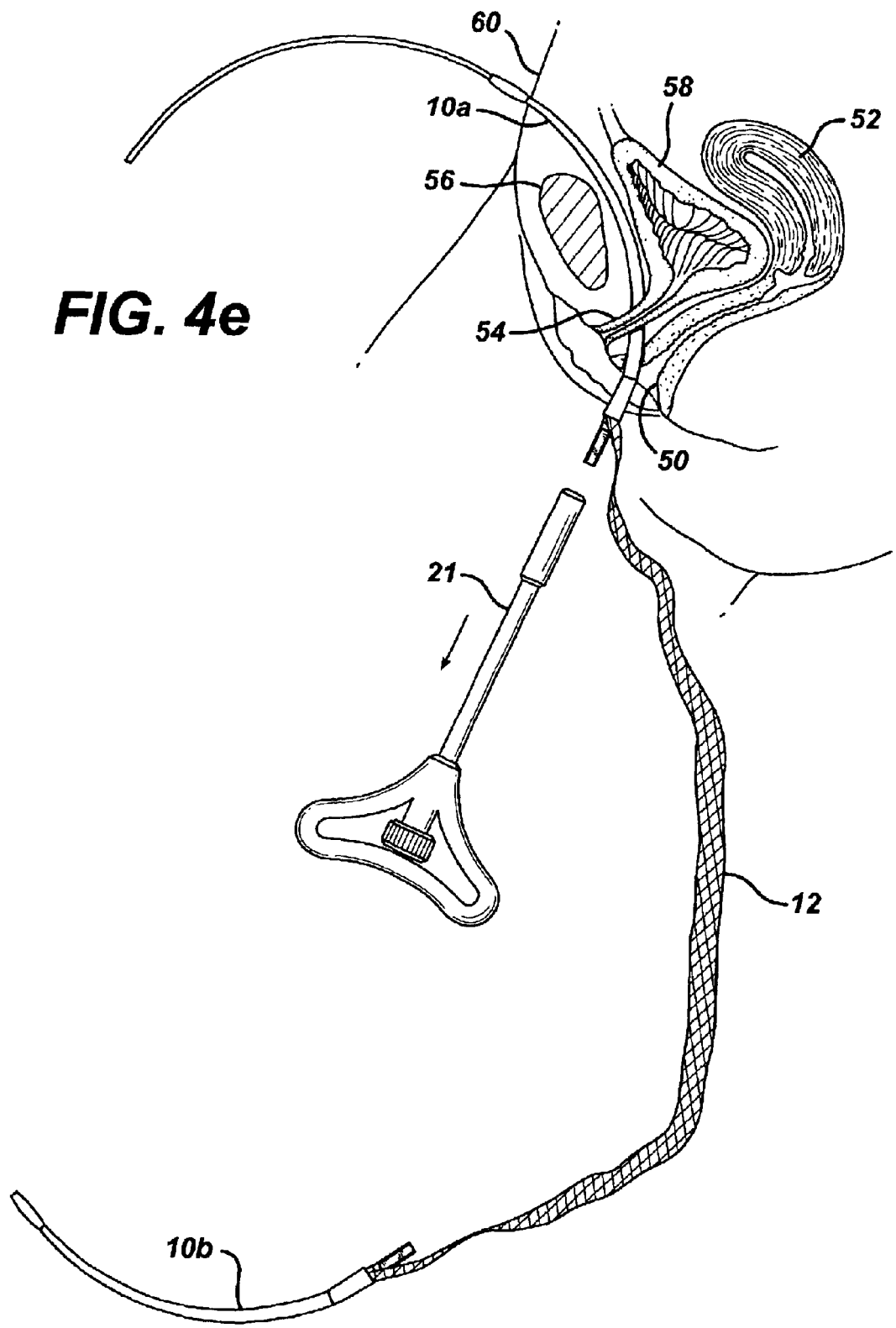
Figure 4F:
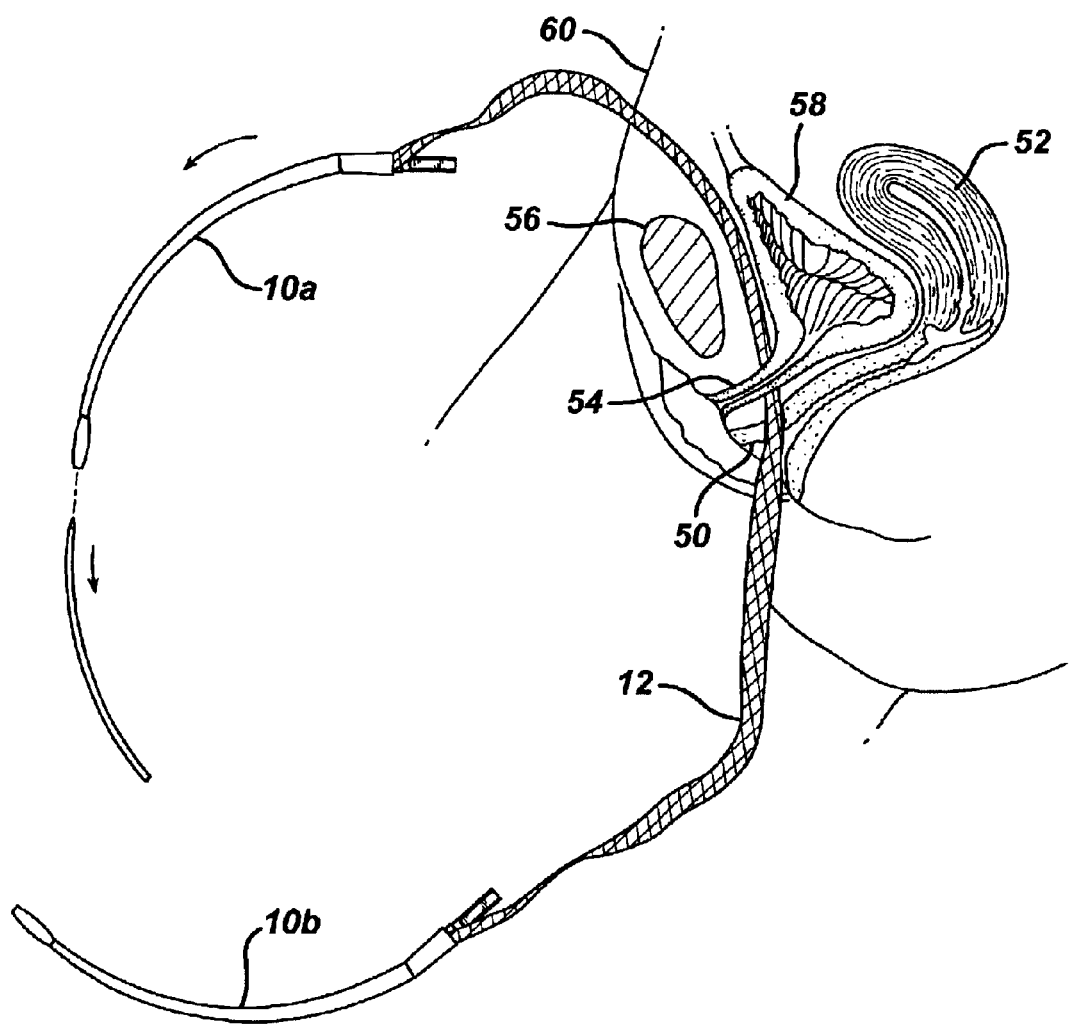
Figure 4G:
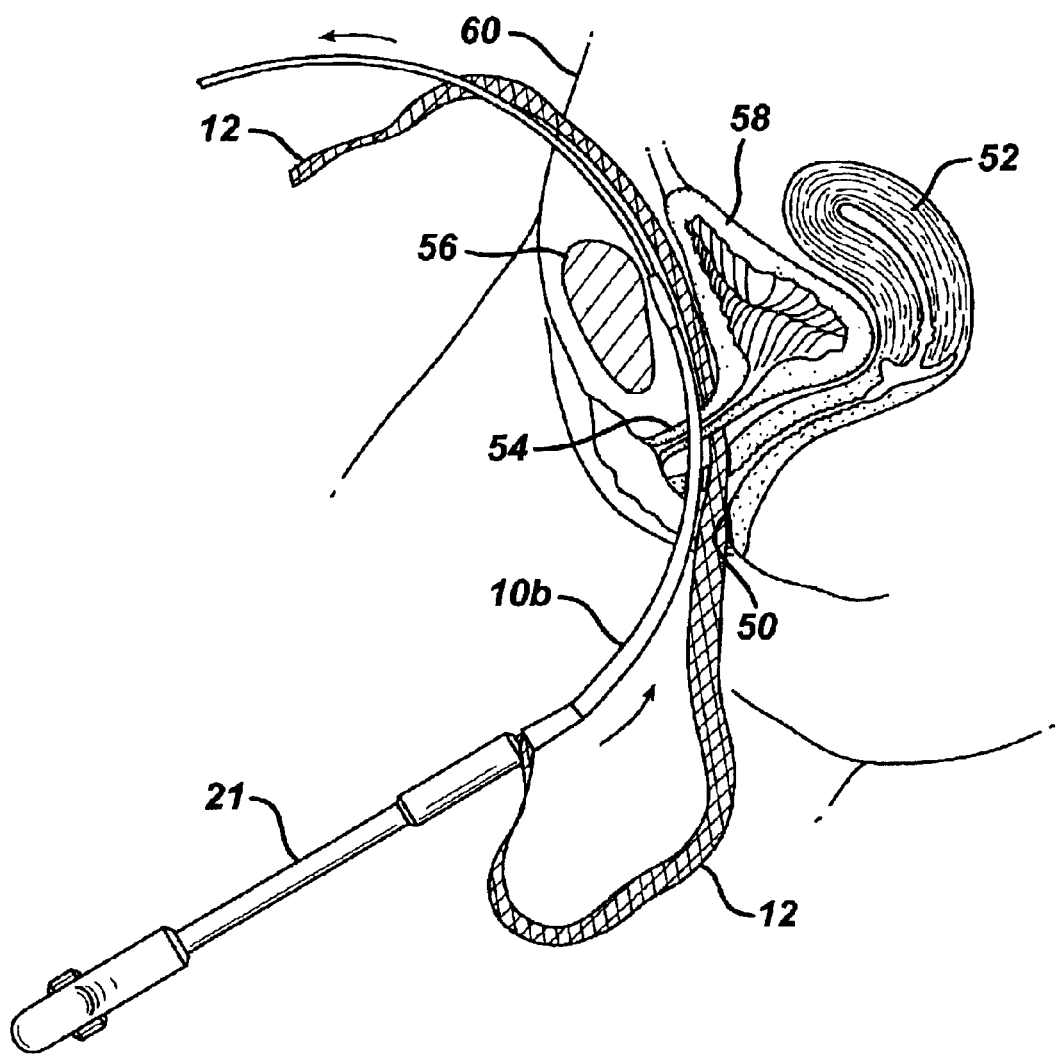
Figure 4H:
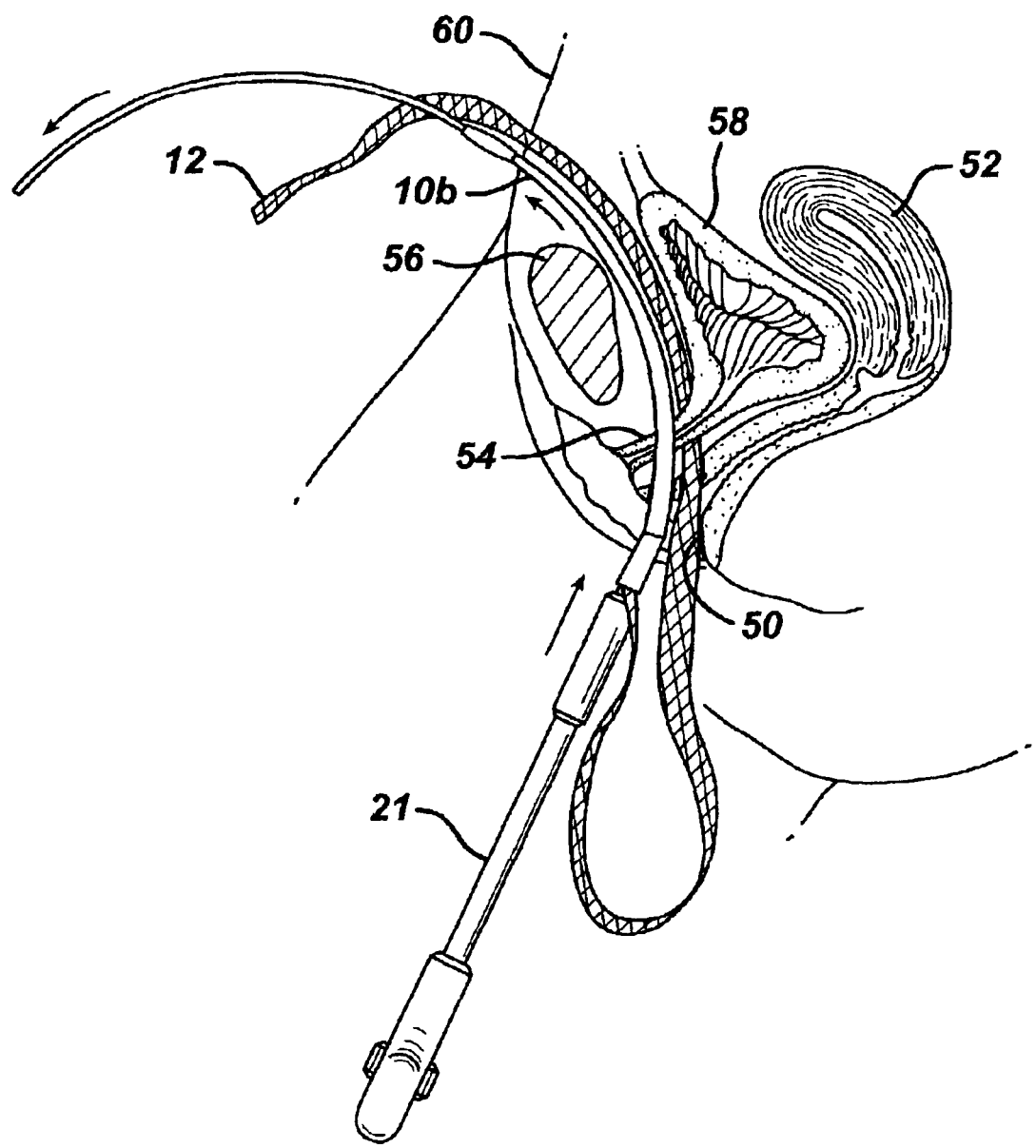
Figure 4I:
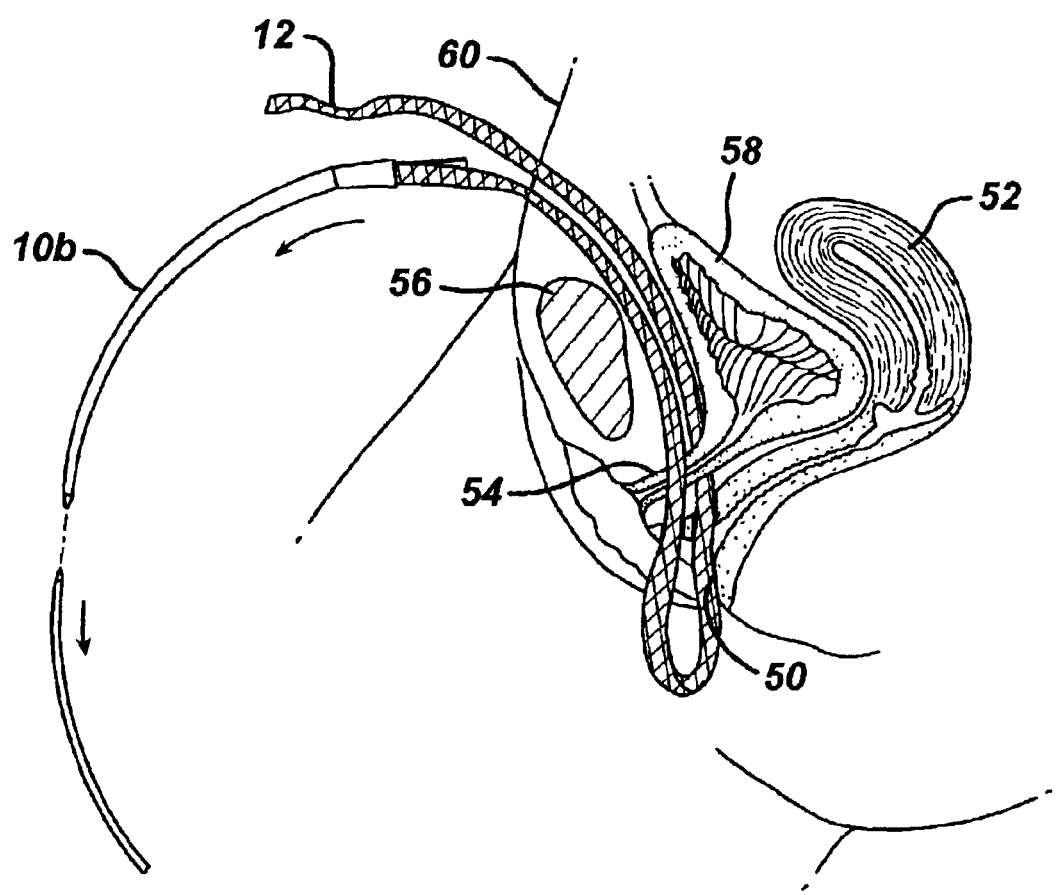
Figure 4J:
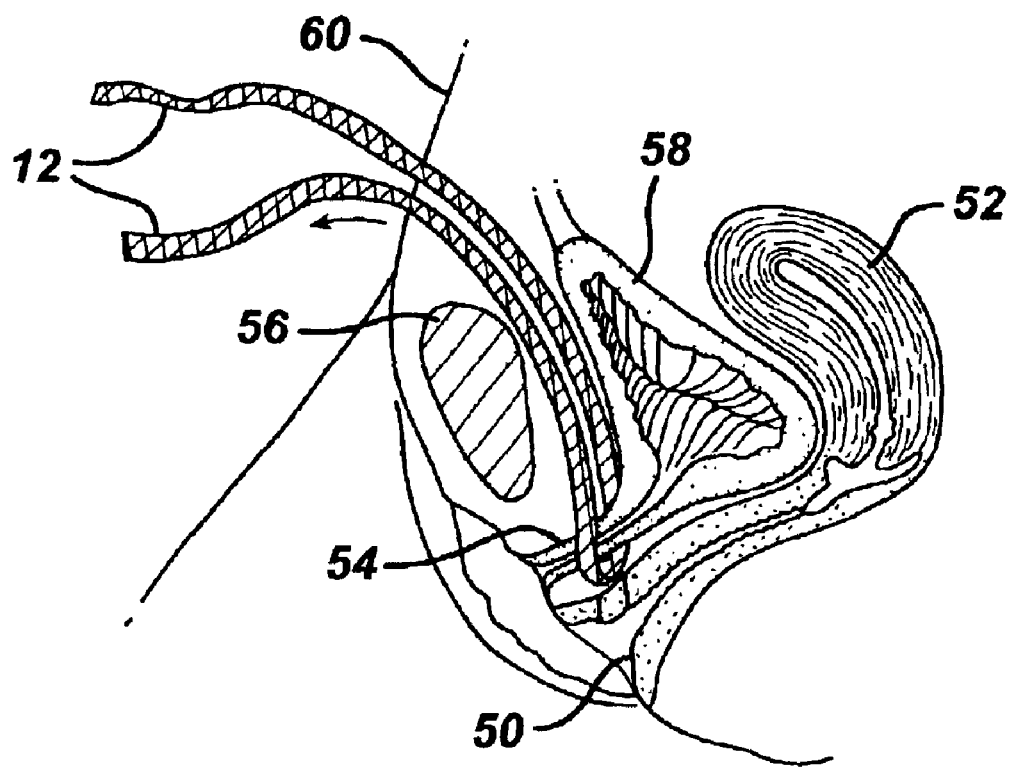
Figure 8B:
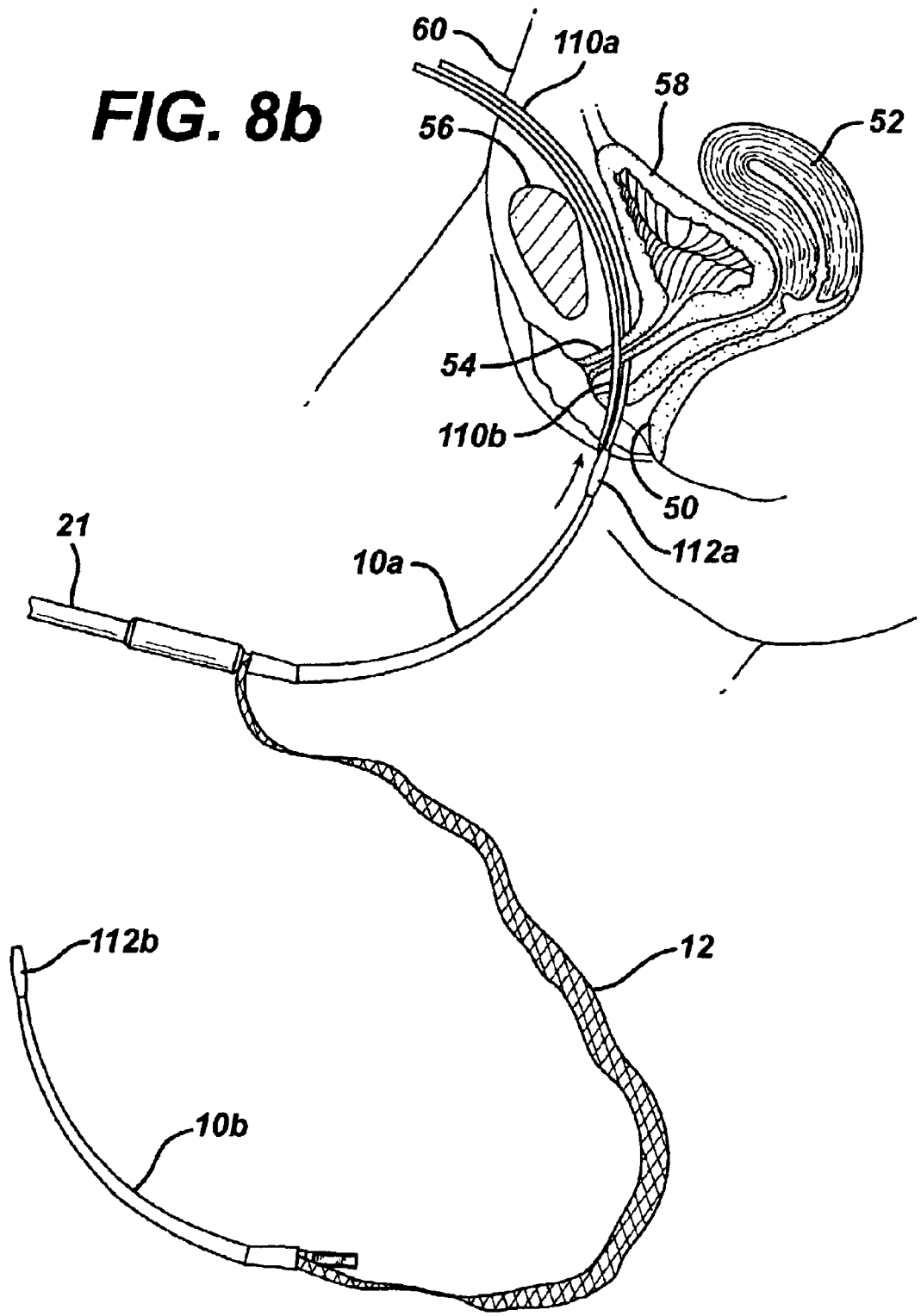
Figure 8D:
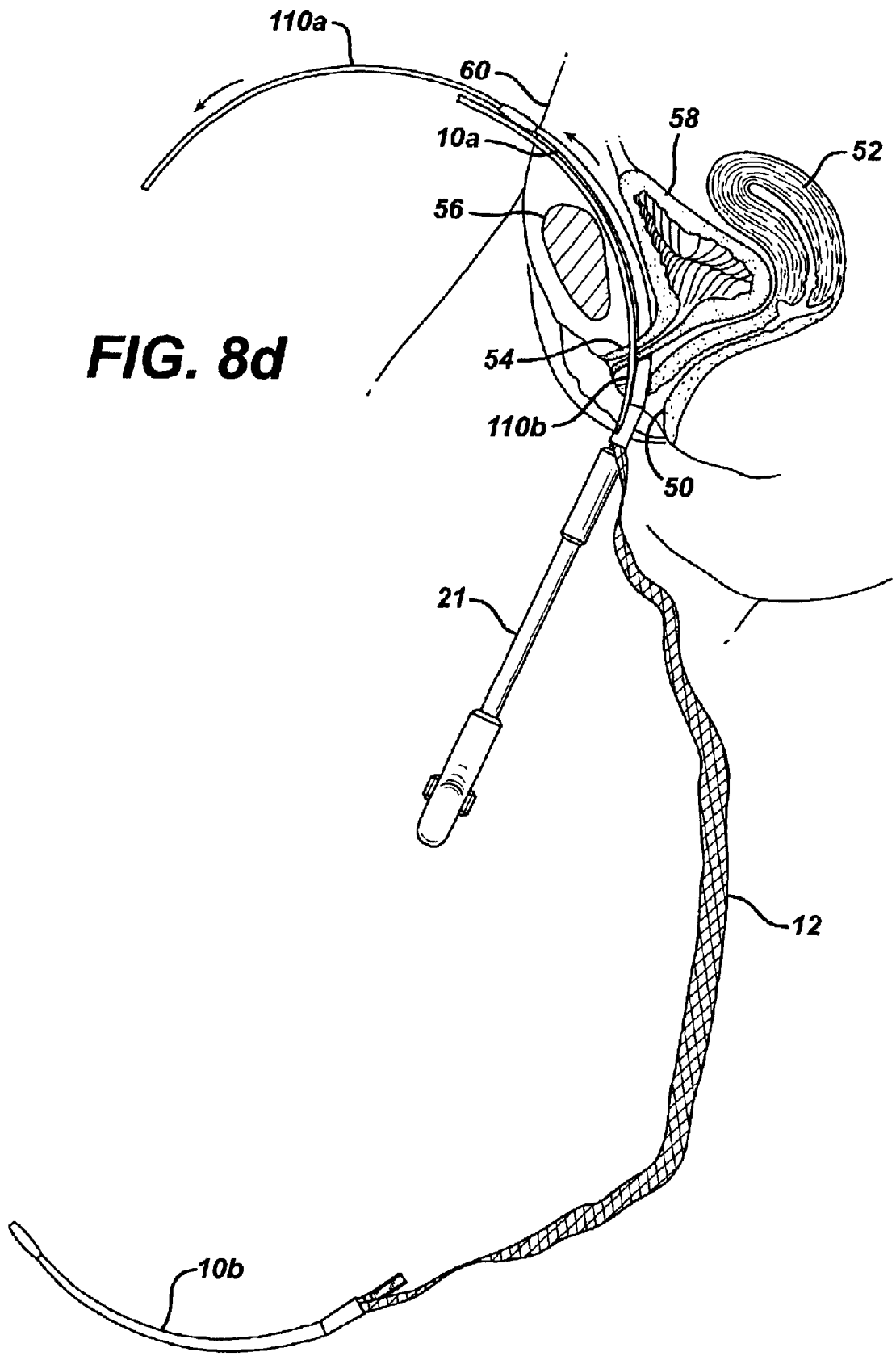
Figure 8E:
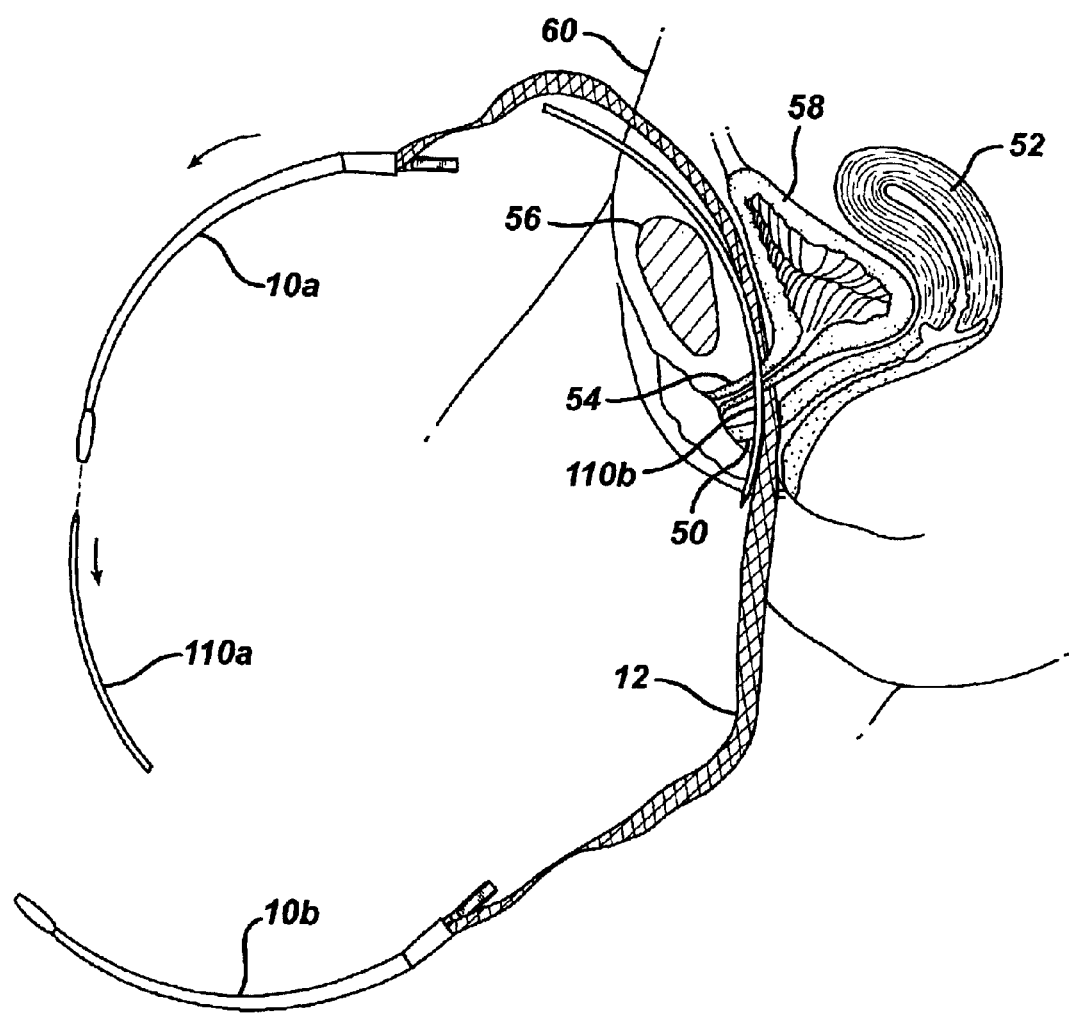
Figure 8F:
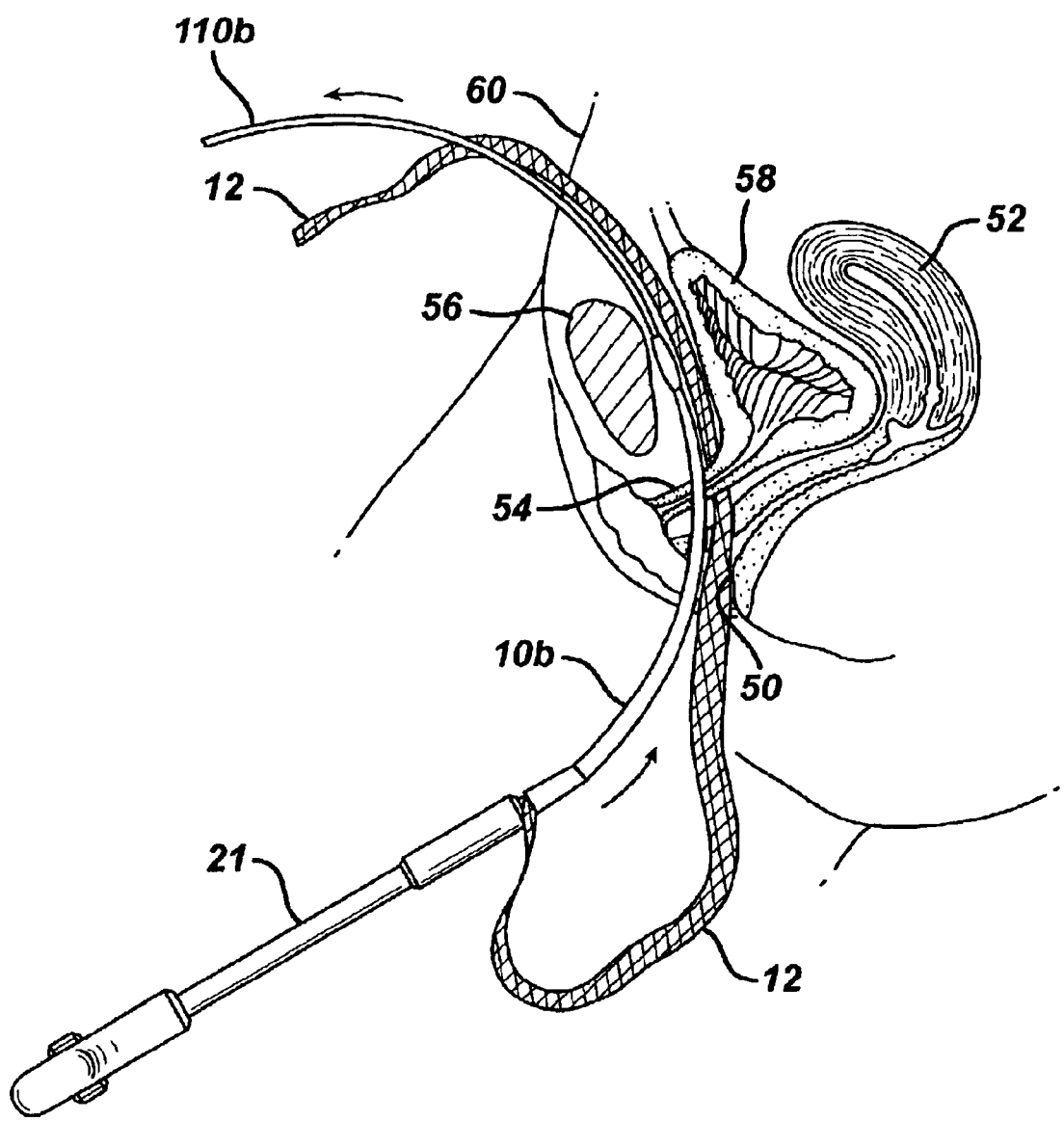
Figure 8G:
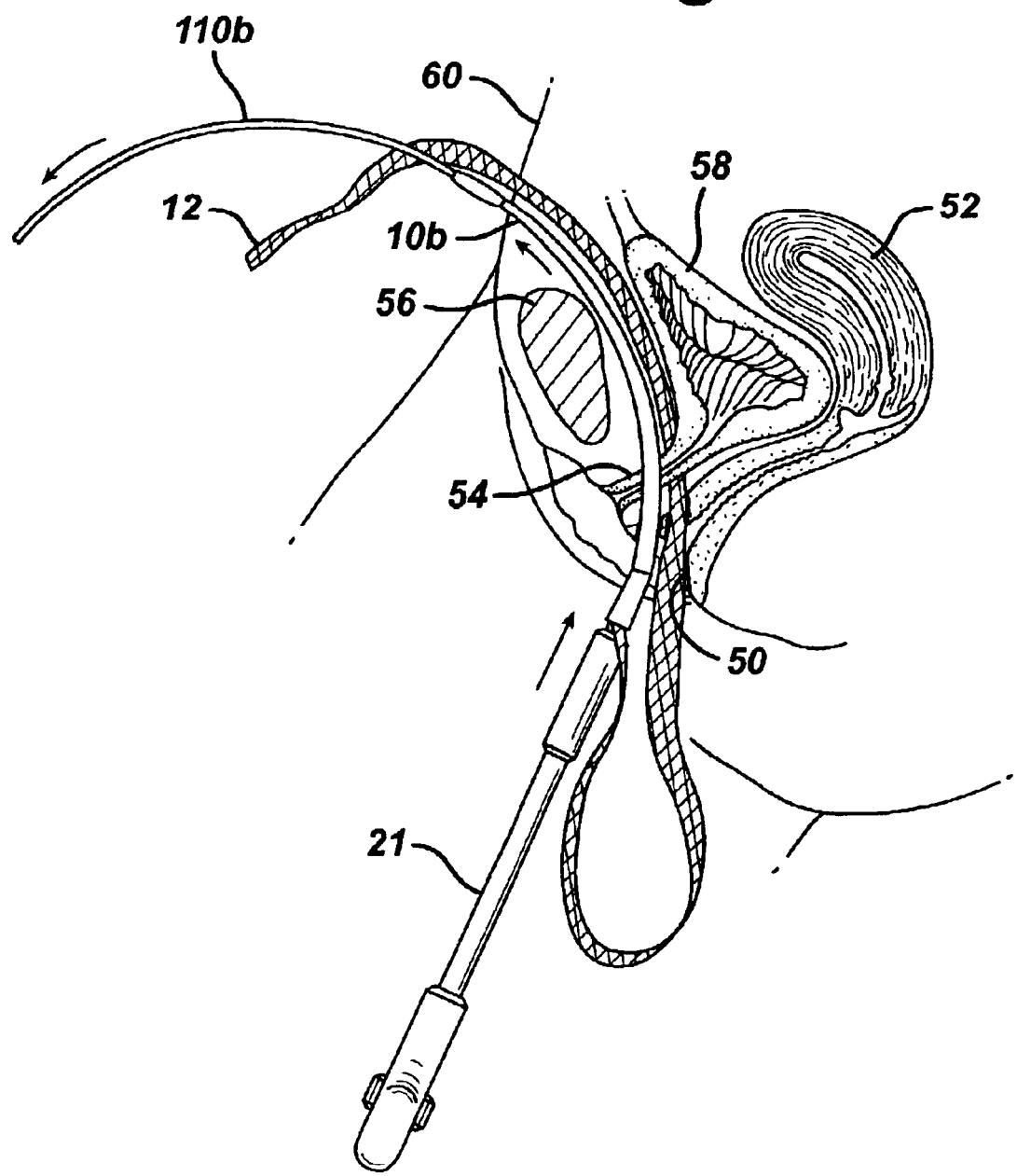
Figure 8H:
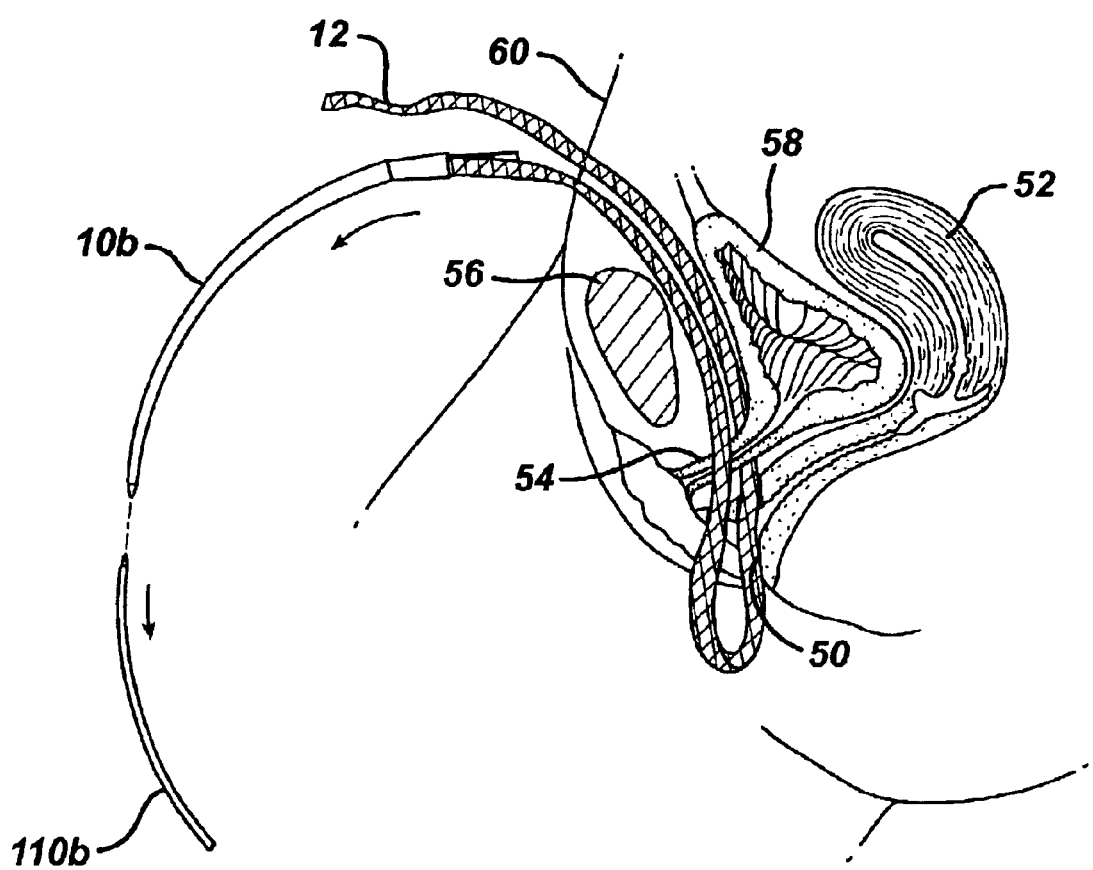
Figure 8I:
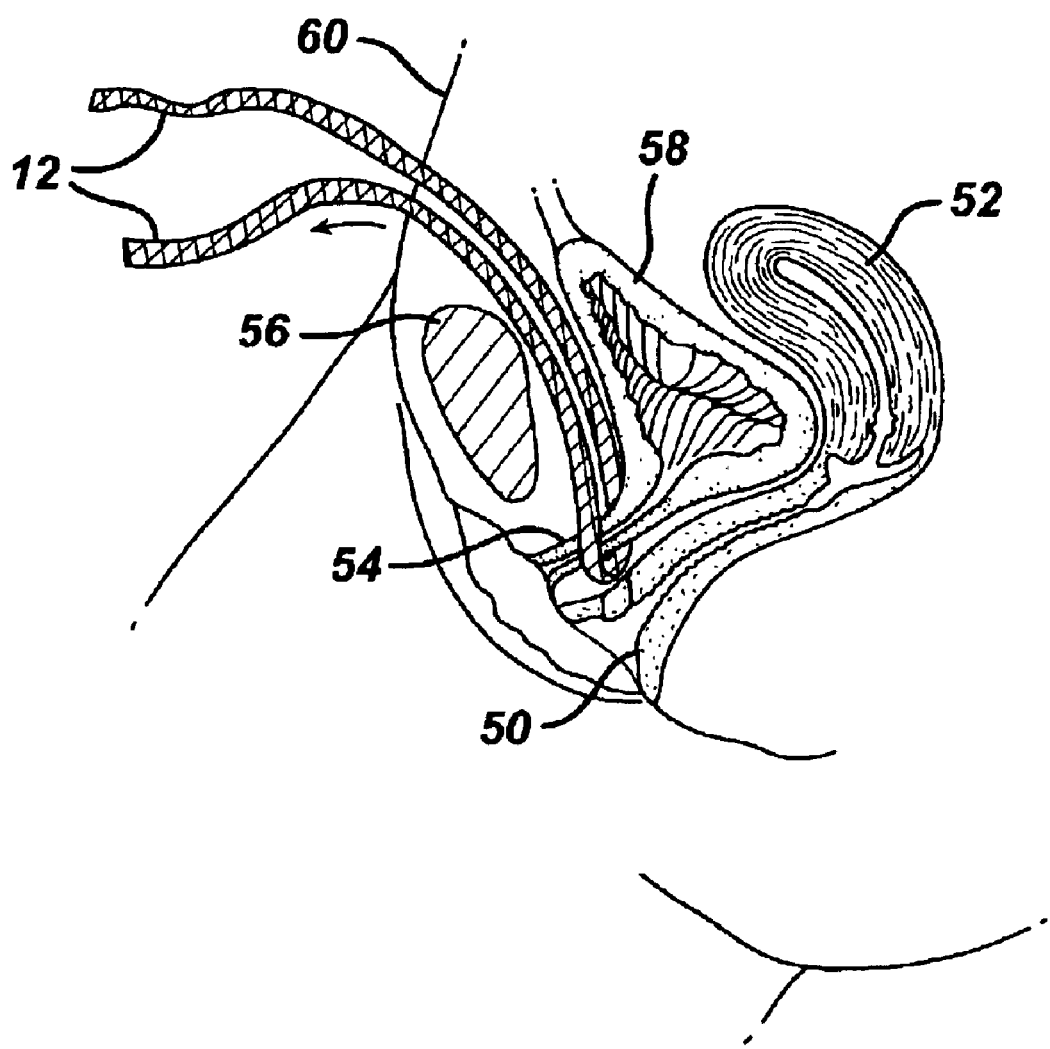

Furthermore, it is possible that the foregoing procedures can be performed such that the needles 10, 10a, 10b and the guide needles 110, 110a are connected to one another at their distal ends within the patient's body (not shown), rather than outside the body proximate to the vagina as shown in the various figures (see, for example, FIGS. 4b, 8b and 9d). As will be obvious to persons of ordinary skill in the art, where is it desired to connect the needles within the patient's body, a guiding or viewing mechanism will have to be provided so that the distal ends of the needles can be properly aligned and connected. Such guiding or viewing mechanisms could include well-known methods such as ultrasound, x-ray or fluorescence. Alternatively, magnets could be provided at the distal ends of the needles to facilitate their alignment with one another. Alternatively, an external mechanical aiming device or an electronic device (such as would indicate in which direction the needles must be moved to align with one another), could be developed and used satisfactorily with one or more embodiments of the present invention described hereinabove.

It will be apparent from the foregoing that, while particular forms of the invention have been illustrated and described, various modifications can be made without departing from the spirit and scope of the invention. Accordingly, it is not intended that the invention be limited to the specific embodiments described hereinabove and illustrated in the figures.

We claim:

1. A surgical instrument for treating a patient suffering from female urinary stress incontinence, comprising:
   a) a tape for implanting into the lower abdomen of a female to provide support to the urethra, said tape having a pair of ends;
   b) a curved anesthesia needle having a curvature and length permitting said curved anesthesia needle to extend along a pathway through the patient's abdominal wall, over the pubic bone, past the urethra and through the vaginal wall, such that anesthesia can be applied by the curved anesthesia needle along the pathway, said curved anesthesia needle also adapted to function as a guide element and having a distal end;
   c) a curved needle element attached to proximate to one end of said tape, said needle element including a curved shaft having a distal; and
   d) connecting means for removably connecting said distal end of said curved anesthesia needle to said distal end of said needle element.

2. The surgical instrument of claim 1, wherein said distal end of said anesthesia needle has a diameter of approximately 2 millimeters.

3. A surgical instrument for treating a patient suffering from female urinary stress incontinence, comprising:
   (a) a tape for implanting into the lower abdomen of a female to provide support to the urethra, said tape having a pair of opposed ends;
   (b) a guide element in the form of an anesthesia needle including means for delivering anesthesia to the patient's body and having a distal end;
   (c) a curved needle element attached proximate to one end of said tape, said needle element including a curved shaft having a distal end; and
   (d) connecting means for removably connecting said distal end of said guide element to said distal end of said needle element, said connecting means having a bore in said distal end of said needle element, said bore being sized and shaped to securely and removably receive said distal end of said anesthesia needle therein.

4. The surgical instrument of claim 3, further comprising another curved needle element attached proximate to an opposite end of said tape, said another needle element including a curved shaft having a distal end; and second connecting means for removably connecting said distal end of said anesthesia needle to said distal end of said another needle element.

5. The surgical instrument of claim 4, wherein said second connecting means includes a bore in said distal end of said another needle element, said bore being sized and shaped to securely and removably receive said distal end of said anesthesia needle therein.

6. The surgical instrument of claim 5, wherein said tape is substantially flat and flexible.

7. An improved surgical instrument for treating a patient suffering from female urinary stress incontinence, including a tape for implanting into the lower abdomen of a female to provide support to the urethra, said tape having a pair of ends; a first curved needle element having a distal end; a second needle element attached proximate to one end of said tape, said second needle element including a curved shaft having a distal end; and connecting means for removably connecting said distal end of said first needle element to said distal end of said second needle element, the improvement wherein said first curved needle element is an anesthesia needle which includes means for delivering anesthesia to the patient's body.

8. A method for treating a patient suffering from female urinary incontinence, comprising the steps of:
   anesthetizing a pathway within the patient's body proximate to the patient's urethra, said pathway extending through the patient's abdominal wall, over the pubic bone, past the urethra, and through the vaginal wall by passing an anesthesia needle with a distal end into the patient's body along said pathway with periodic pauses along said pathway and injecting a clinically effective amount of anesthesia into the patient's body during said periodic pauses such that said pathway is anesthetized;
   passing a tape into the patient's body along said pathway by attaching a first needle having a distal end to one end of the tape; attaching a second needle having a distal end to an opposite end of the tape;
   removably connecting the distal end of the anesthesia needle to the distal end of the first needle;
   withdrawing the anesthesia needle back along said pathway such that the first needle and the one end of the tape are passed through the patient's body along said anesthetized pathway and such that the one end of the tape extends through the abdominal wall and out of the patient's body;
   disconnecting the distal end of the anesthesia needle from the distal end of the first needle;
   passing the anesthesia needle into the patient's body along a second pathway;
   removably connecting the distal end of the anesthesia needle to the distal end of the second needle;
   withdrawing the anesthesia needle back along said second pathway such that the second needle and the opposite end of the tap are passed through the patient's body along said second anesthetized pathway and such that the opposite end of the tape extends through the abdominal wall and out of the patient's body; and
   disconnecting the distal end of the anesthesia needle from the distal end of the second needle; and
   positioning at least a portion of the tape between the vaginal wall and the urethra such that the tape forms a supportive loop beneath the urethra.

9. The method of claim 8, further comprising the step of adjusting the position and tension of the supportive loop to achieve a clinically acceptable degree of urinary continence.

10. A method for treating a patient suffering from female urinary incontinence, comprising the steps of:
- anesthetizing a pathway extending through the patient's abdominal wall, over the pubic bone, past the urethra, and through the vaginal wall by inserting a curved anesthesia needle into the patient's body periodically pausing and injecting anesthetic during said pauses, said curved anesthesia needle extending along said pathway and injecting a clinically effective amount of anesthesia into the patient's body as curved anesthesia needle traverses the pathway;
- removably attaching a needle having a distal end to one end of a tape
- passing the tape into the patient's body along said pathway using the curved anesthesia needle as a guide element, such that when the curved anesthesia needle traverses the pathway, the tape follows the needle and the curved aneshthesia needle along the pathway; and
- positioning at least a portion of the tape between the vaginal wall and the urethra such that the tape forms a supportive loop beneath the urethra.

11. A method for treating a patient suffering from female urinary incontinence, comprising the steps of:
- anesthetizing a pathway within the patient's body proximate to the patient's urethra said pathway extending through the patient's abdominal wall, over the pubic bone, past the urethra, and through the vaginal wall by passing an anesthesia needle with a distal end into the patient's body along said pathway with periodic pauses alone said pathway and injecting a clinically effective amount of anesthesia into the patient's body during said periodic pauses such that said pathway is anesthetized;
- passing a tape having a pair of opposed ends into the patient's body along said pathway by removably attaching a needle having a distal end to one end of the tape;
- removably connecting the distal end of the anesthesia needle to the distal end of the needle;
- withdrawing the anesthesia needle back along said pathway such that the needle and the one end of the tape are passed through the patient's body along said anesthetized pathway and such that the one end of the tape extends through the abdominal wall and out of the patient's body;
- disconnecting the distal end of the anesthesia needle from the distal end of the needle and disconnecting the needle from the one end of the tape;
- removably connecting the needle to an opposite end of the tape;
- passing the anesthesia needle into the patient's body along a second pathway;
- removably connecting the distal end of the anesthesia needle to the distal end of the needle;
- withdrawing the anesthesia needle back along said second pathway such that the needle and the opposite end of the tape are passed through the patient's body along said second anesthetized pathway and such that the opposite end of the tape extends through the abdominal wall and of the patient's body;
- disconnecting the distal end of the anesthesia needle from the distal end of the needle; and
- positioning at least a portion of the tape between the vaginal wall and the urethra such that the tape forms a supportive loop beneath the urethra.

12. The method of claim 11, further comprising the step of adjusting the position and tension of the supportive loop to achieve a clinically acceptable degree of urinary continence.

13. A surgical instrument for treating a patient suffering from female urinary stress incontinence, comprising:
- (a) a tape including a natural material for implanting into the lower abdomen of a female to provide support to the urethra, said tape having a pair of opposed ends made of a synthetic material;
- (b) a guide element including means for delivering anesthesia to the patient's body
- (c) a curved needle element attahed proximate to one end of said tape, said needle element including a curved shaft having a distal end; and
- (d) connecting means for removably connecting a distal end of said guide element to said distal end of said needle element.

14. The surgical instrument of claim 13, wherein said natural material is selected from the group consisting of autologous, allograft, xenograft and a tissue engineered matrix.

15. A method for treating a patient suffering from female urinary incontinence, comprising the steps of:
- anesthetizing a pathway within the patient's body proximate to the patient's urethra said pathway extending through the patient's abdominal wall, over the pubic bone, past the urethra, and through the vaginal wall by passing an anesthesia needle with a distal end into the patient's body along said pathway with periodic pauses along said pathway and injecting a clincally effective amount of anesthesia into the patient's body during said periodic pauses such that said pathway is anesthetized;
- passing a tape having a pair of opposed ends into the patient's body along said pathway by removably connecting the distal end of the anesthesia needle to one end of the tape, the pair of opposed ends being made of a synthetic material and the tape including a natural material between the pair of opposed ends;
- withdrawing the anesthesia needle back along said pathway such that the one end of the tape is passed through the patient's body along said anesthetized pathway and extends through the abdominal wall and out of the patient's body;
- disconnecting the distal end of the anesthesia needle from the one end of the tape;
- passing the anesthesia needle again into the patient's body along said pathway;
- removably connecting the distal end of the anesthesia needle to an opposite end of the tape;
- withdrawing the anesthesia needle back along said pathway such that the opposite end of the tape is passed through the patient's body along said anesthetized pathway and extends through the abdominal wall and out of the patient's body;
- positioning at least a portion of the tape between the vaginal wall and the urethra such that the tape forms a supportive loop beneath the urethra said positioning step being performed so that the natural material is positioned beneath the urethra; and
- disconnecting the distal end of the anesthesia needle from the opposite end of the tape.

16. The method of claim 15, further comprising the step of adjusting the position and tension of the supportive loop to achieve a clinically acceptable degree of urinary continence. issue engineered matrix.

* * * * *

UNITED STATES PATENT AND TRADEMARK OFFICE
CERTIFICATE OF CORRECTION

PATENT NO. : 6,932,759 B2
DATED : August 23, 2005
INVENTOR(S) : Gene W. Kammerer et al.

It is certified that error appears in the above-identified patent and that said Letters Patent is hereby corrected as shown below:

Column 11,
Line 43, after "distal" insert -- end --.

Column 13,
Line 13, after "as" insert -- said --.
Line 33, "alone" should read -- along --.
Line 62, after "and" insert -- out --.

Column 14,
Line 13, "attahed" should read -- attached --.
Line 65, delete "issue engineered matrix.".

Signed and Sealed this

Fifteenth Day of November, 2005

JON W. DUDAS
*Director of the United States Patent and Trademark Office*